United States Patent
Natsugari et al.

[11] Patent Number: 5,929,107
[45] Date of Patent: Jul. 27, 1999

[54] CONDENSED HETEROCYCLIC COMPOUNDS, THEIR PRODUCTION AND USE

[75] Inventors: Hideaki Natsugari, Ashiya; Yasuo Sugiyama, Kawanishi; Yoshinori Ikeura, Koryo-cho, all of Japan

[73] Assignee: Takeda Chemical Industries, Ltd., Osaka, Japan

[*] Notice: Under 35 U.S.C. 154(b), the term of this patent shall be extended for 198 days.

[21] Appl. No.: 08/554,228

[22] Filed: Nov. 8, 1995

Related U.S. Application Data

[62] Division of application No. 08/165,925, Dec. 14, 1993, Pat. No. 5,492,929.

[30] Foreign Application Priority Data

Dec. 16, 1992 [JP] Japan .................................. 4-336312
Oct. 4, 1993 [JP] Japan .................................. 5-248069

[51] Int. Cl.$^6$ .................. A61K 31/38; C07D 333/58; C07D 333/66
[52] U.S. Cl. .................. 514/443; 549/57; 549/58
[58] Field of Search .................. 549/57, 58; 514/443

[56] References Cited

U.S. PATENT DOCUMENTS

| | | | |
|---|---|---|---|
| 3,944,672 | 3/1976 | Steinman | 424/274 |
| 4,054,585 | 10/1977 | Felauer et al. | 544/152 X |
| 4,113,731 | 9/1978 | Winters et al. | 260/288 |
| 5,464,863 | 11/1995 | Nagamine et al. | 514/443 |

FOREIGN PATENT DOCUMENTS

| | | |
|---|---|---|
| 0 135 770 | 4/1985 | European Pat. Off. |
| 0 512 570 | 11/1992 | European Pat. Off. |
| 0 613 894 | 9/1994 | European Pat. Off. |

OTHER PUBLICATIONS

Winters et al., Synthesis and Biological Activities of Some Indolo [2,3–C] Isoquinoline Derivatives, I1 Farmaco—Ed. Sc. vol. 34(6), 1978, pp. 507–517.
Chemical Abstracts vol. 117, No. 48431C, 1992.
Chatterjea et al., "Synthesis of Furano Compounds", J. Indian Chem. Soc., vol. LIII (1976), pp. 295–299.
Chatterjea et al., "Experiments on the Synthesis of Furano Compounds", J. Indian Chem. Soc., vol. 33(5), 1956, pp. 339–345.

*Primary Examiner*—Laura L. Stockton
*Attorney, Agent, or Firm*—Foley & Lardner

[57] ABSTRACT

Novel compound represented by the formula:

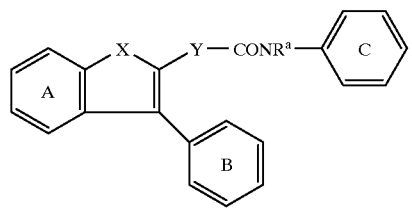

wherein ring A, ring B and ring C each stands for an optionally substituted benzene ring; X stands for —NR— wherein R stands for hydrogen atom or an optionally substituted hydrocarbon group, —O— or —S—; Y stands for —(CH$_2$)n— wherein n denotes 1 or 2 or —NH—; and R$^a$ stands for a hydrogen atom or an optionally substituted hydrocarbon group, provided that when ring C is unsubstituted or substituted only at para-position, ring B is substituted at least at ortho-position or a salt thereof which have an excellent acyl-CoA: cholesterol acyltransferase inhibiting action and cholesterol-lowering activity, their production and medicinal use.

16 Claims, No Drawings

CONDENSED HETEROCYCLIC COMPOUNDS, THEIR PRODUCTION AND USE

This application is a division of application Ser. No. 08/165,925, filed Dec. 14, 1993, now U.S. Pat. No. 5,492,929.

The present invention relates to a novel condensed heterocyclic compound having an excellent acyl-CoA:cholesterol acyltransferase (ACAT) inhibiting action and cholesterol-lowering activity.

As compounds which contain a phenyl group and —Y—CONH—Ph (Ph means a phenyl group), wherein Y stands for —(CH$_2$)n— (n denotes 1 or 2) or —NH—, are substituted adjoining each other at the heterocyclic portion of the condensed ring consisting of 5-membered heterocyclic ring and benzene ring, have been known, for example, (1) a compound represented by the formula:

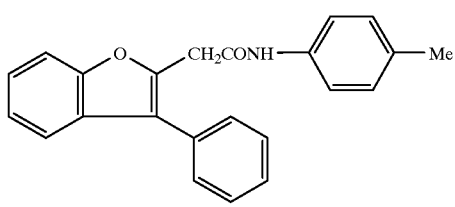

disclosed in Journal of Indian Chemical Society, 33, pp 339–345 (1956), (2) a compound represented by the formula:

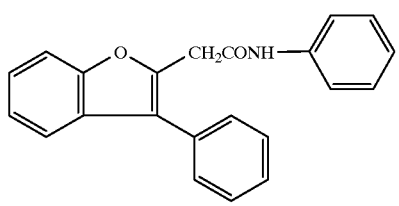

disclosed in Journal of Indian Chemical Society, 53, pp 295–299 (1976), (3) a compound represented by the formula:

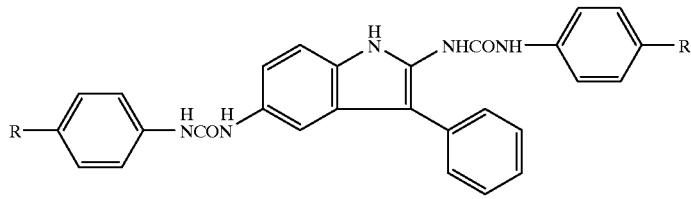

wherein R stands for chlorine atom or methoxy group disclosed in Chemical Abstract, 117, 48431c, and (4) a compound represented by the formula:

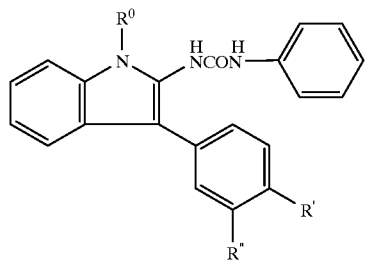

wherein R⁰, R' and R" respectively stand for

TABLE 1

| R⁰ | R' | R" |
|----|-----|-----|
| Me | MeO | H |
| Me | Me | H |
| Me | iso-Pr | H |
| Me | Cl | H |
| Me | MeO | MeO |
| Me | H | H |
| H | H | H | in Table 1, H stands for hydrogen atom, Me stands for methyl group, MeO stands for methoxy group, iso-Pr stands for isopropyl group, and Cl stands for chlorine atom, disclosed in Farmaco, Edizione Scientifica, 34, pp 507–517 (1979).

Separately from the above compounds, compounds which have

(A is a bond or lower alkylene) instead of —Y—CONH— and H, optionally substituted alkyl or cycloalkyl group instead of the phenyl group in the moiety —Y—CONH—Ph, represented by the formula:

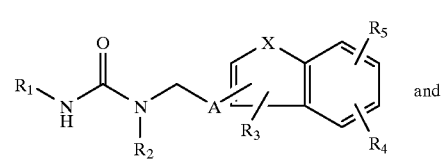 (a)

and

-continued

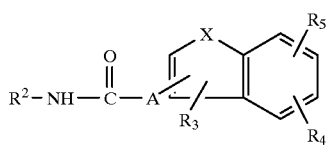

(b)

respectively, wherein $R_1$=aryl optionally substituted by halo, $NO_2$, $NH_2$ or lower alkylamino, alkoxy or acylamino;

$R_2$=H, alkyl, cycloalkyl or lower alkyl optionally substituted by cyclo(lower)alkyl, cyclo(lower)alkenyl, heterocyclyl or aryl (optionally substituted);

$R_3$=H, lower alkyl or aryl (optionally substituted by halo, $NO_2$, $NH_2$ or lower alkylamino);

$R_4$=H, halo, lower alkyl or alkoxy or aryl (optionally substituted by halo);

$R_5$=H, halo, lower alkyl or aryl; and A=single bond or lower alkylene; X=O, S or NH;

provided that when $R_2$ is cycloalkyl, then $R_3$ is aryl or $R_4$ is halo, lower alkoxy or aryl, are disclosed in EP-512570-A1 (Publication Date: Nov. 11, 1992).

Among these known literature references, while (3) refers to antimicrobial action of the compound, (1), (2) and (4) refer to only the synthesis of the compound and physicochemical properties of the compound, but no reference to its action is made. With respect to these compounds, no reports have been made so far whether or not they have an ACAT inhibiting action, an action of lowering cholesterol level in blood or a therapeutic action of arteriosclerosis. On the other hand, the EP-512570-A1 reference discloses the compound (a) having an ACAT inhibitory action and the compound (b) as an intermediate to produce the compound (a).

Circumstances being such as above, development of a compound having an excellent ACAT inhibiting action, inhibiting, in mammals, absorption of cholesterol from intestinal tube and accumulation of cholesterol ester at the wall of artery and useful as prophylactic/therapeutic agents of hypercholesterolemia, atherosclerosis and various diseases caused by them (e.g. ischemic heart diseases such as myocardial infarction, and, disorders of cerebral blood vessel such as cerebral infarction and cerebral apoplexy) has been desired.

The present inventors made extensive studies on compound having condensed 5-membered cyclic structure and found that the novel compound (I) of the formula:

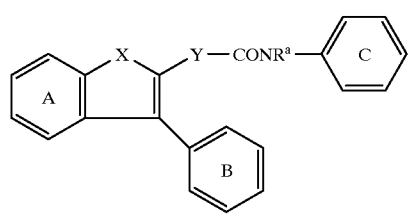

(I)

wherein ring A, ring B and ring C each stands for an optionally substituted benzene ring; X stands for —NR— wherein R stands for hydrogen atom or an optionally substituted hydrocarbon group, —O— or —S—; Y stands for —$(CH_2)n$— wherein n denotes 1 or 2, or —NH—; and $R^a$ stands for a hydrogen atom or an optionally substituted hydrocarbon group, provided that when ring C is unsubstituted or substituted only at para-position, ring B is substituted at least at ortho-position and a compound (I"), including the novel compound (I), of the formula:

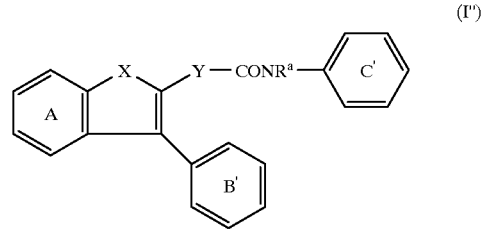

(I")

wherein ring A, ring B' and ring C' each stands for an optionally substituted benzene ring; X stands for —NR— wherein R stands for hydrogen atom or an optionally substituted hydrocarbon group, —O— or —S—; Y stands for —$(CH_2)n$— wherein n denotes 1 or 2, or —NH—: and $R^a$ stands for a hydrogen atom or an optionally substituted hydrocarbon group, and a salt thereof show, unexpectedly, strong ACAT inhibiting actions, and are useful as a safely administrable cholesterol lowering agent or a therapeutic agent of arteriosclerosis.

The above compounds (I") or a salt thereof can be produced by the methods of (1) or (2).

(1) A process for producing a compound (I") or a salt thereof, which comprises reacting a compound (II) represented by the formula:

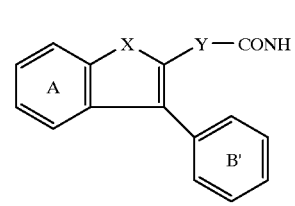

(II)

wherein all symbols are of the same meanings as defined hereinabove or a salt or reactive derivative thereof with a compound (III) represented by the formula:

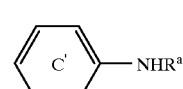

(III)

wherein the symbols are of the same meanings as defined hereinabove or a salt thereof, (2) A process for producing a compound (I') represented by the formula:

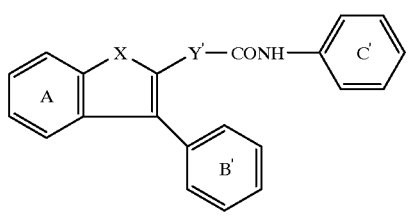

(I')

wherein Y' stands for —NH—, and the other symbols are of the same meanings as defined hereinabove, which comprises reacting a compound (IV) represented by the formula:

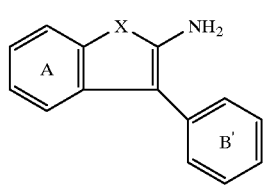

(IV)

wherein all symbols are of the same meanings as defined hereinabove or a salt thereof with a compound (V) represented by the formula:

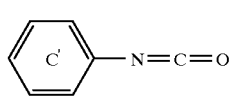

(V)

wherein the symbol is of the same meaning as defined hereinabove.

In the above-mentioned formula, ring A, ring B, ring B', ring C and ring C' respectively stand for an optionally substituted benzene ring. Examples of substituents include a halogen atom (e.g. fluorine, chlorine, iodine, etc., preferably fluorine, chlorine), an optionally halogenated alkyl group, an optionally halogenated alkoxy group, an optionally halogenated alkylthio group, a $C_{1-7}$ acylamino group (e.g. formylamino, acetylamino, propionylamino, butyrylamino, benzoylamino, etc.), an amino group, a mono- or di-$C_{1-4}$ alkylamino group (e.g. methylamino, ethylamino, propylamino, dimethylamino, methylethylamino, methyl propylamino, etc.), a $C_{1-3}$ acyloxy group (e.g. formyloxy, acetoxy, propionyloxy etc.), a hydroxyl group, a cyano group, a carboxyl group, etc.

As the above-mentioned optionally halogented alkyl group, use is made of, for example, a $C_{1-6}$ straight-chain or branched alkyl group or this alkyl having one to five halogen atoms as substituents (e.g. fluorine, chlorine, bromine and iodine, preferably fluorine and chlorine), and use is often made of, for example, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl and 5-trifluoromethylpentyl, preferably, for example, $C_{1-4}$ straight-chain or branched alkyl groups including methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, butyl, 4,4,4-trifluorobutyl, isobutyl, sec-butyl, tert-butyl, or such an alkyl group as above on which one to three halogen atoms may be substituted.

As the optionally halogenated alkoxy group, use is made of, for example, a $C_{1-6}$ straight-chain or branched alkoxy group or the one on which one to five halogen atoms as mentioned above are substituted. As such alkoxy groups as above, use is often made of, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentoxy and hexyloxy, preferably, $C_{1-4}$ straight-chain or branched alkoxy groups, for example, methoxy, difluoromethoxy, trifluoromethoxy, ethoxy, 2,2,2-trifluoroethoxy, propoxy, isopropoxy, butoxy, 4,4,4-trifluorobutoxy and sec-butoxy, or these alkoxy groups on which one to three halogen atoms as mentioned above may be substituted.

As the optionally halogenated alkylthio group use is made of, for example, a $C_{1-6}$ straight-chain or branched alkylthio group or the one on which one to five halogen atoms as mentioned above are substituted. As such alkylthio groups as above, use is often made of, for example, methylthio, difluoromethylthio, trifluoromethylthio, ethylthio, propylthio, isopropylthio, butylthio, 4,4,4-trifluorobutylthio, pentylthio and hexylthio, preferably, $C_{1-4}$ straight-chain or branched alkylthio groups, for example, methylthio, difluoromethylthio, trifluoromethylthio, ethylthio, propylthio, butylthio and 4,4,4-trifluorobutylthio or the one on which one to three halogen atoms as mentioned above may be substituted.

Preferable examples of the substituents on ring A, ring B, ring B', ring C or ring C' include (i) a halogen atom, (ii) an optionally halogenated $C_{1-6}$ alkyl group, (iii) an optionally halogenated $C_{1-6}$ alkoxy group, (iv) a hydroxyl group, (v) an amino group, (vi) a mono- or di-$C_{1-4}$ alkylamino group or (vii) a $C_{1-3}$ acyloxy group.

Concrete examples of groups (i) to (vii) have the same meanings as defined hereinabove.

The substituents on ring A, ring B, ring B', ring C and ring C' may be substituted on any possible position of the ring, and two or more of such substituents may be the same or different, and the number of such substituents ranges from one to four, preferably one or two. And, the carbons adjacent to each other on ring A, ring B, ring C or ring C' may be bonded to a group represented by —$(CH_2)_1$—, wherein 1 denotes an integer of 3 to 5, to form a 5- to 7-membered ring, and these cases are also included in the object compounds (I) or (I").

As preferable examples of ring A, use is made of a benzene ring optionally substituted with one to four, preferably one or two, substituents selected from, for example a halogen atom (e.g. fluorine, chlorine, bromine, etc.), an optionally halogenated $C_{1-4}$ alkyl group (e.g. methyl, ethyl, isopropyl, trifluoromethyl, etc.) and an optionally halogenated $C_{1-4}$ alkoxy group (e.g. methoxy, ethoxy, isopropoxy, trifluoromethoxy etc.). For example, the ring A includes preferably an optionally substituted benzene ring represented by the formula [A]:

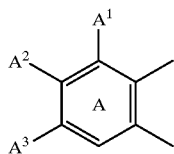

wherein $A^1$, $A^2$ and $A^3$ independently stand for a hydrogen atom, a halogen atom (e.g. fluorine, chlorine, etc.), an optionally halogenated $C_{1-4}$ alkyl group (e.g. methyl, ethyl, isopropyl, trifluoromethyl, etc.) or an optionally halogenated $C_{1-4}$ alkoxy group (e.g. methoxy, ethoxy, isopropoxy, trifluoromethoxy, etc.). More preferably, the ring A includes optionally substituted benzene rings of formula [A], wherein (1) $A^1$, $A^2$ and $A^3$ are all hydrogen atom, (2) $A^1$ and $A^2$ are both hydrogen, and $A^3$ is a halogen atom, an optionally halogenated $C_{1-4}$ alkyl group or an optionally halogenated $C_{1-4}$ alkoxy group, (3) $A^1$ is hydrogen, $A^2$ and $A^3$ are independently a halogen atom, an optionally halogenated $C_{1-4}$ alkyl group or an optionally halogenated $C_{1-4}$ alkoxy group, (4) $A^2$ is hydrogen, $A^1$ and $A^3$ are independently an optionally halogenated $C_{1-4}$ alkyl group, or (5) $A^1$ and $A^2$ are both a hydrogen atom, and $A^3$ is a halogen atom.

Concrete examples of the atoms and groups in the above items (1) to (5) have the same meanings as defined hereinabove.

Preferred examples of ring A include optionally substituted benzene rings of the above formula [A] wherein (a) $A^1$, $A^2$ and $A^3$ are all hydrogen, (b) $A^1$ and $A^2$ are both hydrogen, and $A^3$ is chlorine, methyl, ethyl, isopropyl, methoxy or trifluoromethyl group, (c) $A^1$ is hydrogen, $A^2$ and $A^3$ are both methyl or methoxy group, (d) $A^2$ is hydrogen, and $A^1$ and $A^3$ are both methyl group, or (e) $A^1$ and $A^2$ are both hydrogen, and $A^3$ is chlorine.

As preferable ring B or ring B' substituents, use is made of, for example, a benzene ring optionally substituted with one to four, preferable one or two substituents selected from a halogen atom (e.g. fluorine, chlorine, bromine, etc.), an optionally halogenated $C_{1-4}$ alkyl group (e.g. methyl, ethyl, isopropyl, trifluoromethyl etc.) or an optionally halogenated $C_{1-4}$ alkoxy group (e.g. methoxy, ethoxy, isopropoxy, trifluoromethoxy, etc.), more preferably a benzene ring having a substituent at least on the ortho-position. For example, the ring B includes preferably an optionally substituted benzene ring represented by the formula [B]:

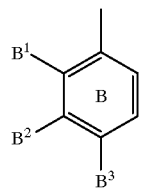

wherein $B^1$, $B^2$ and $B^3$ independently stand for a hydrogen atom, a halogen atom (e.g. fluorine, chlorine, bromine, etc.), an optionally halogenated $C_{1-4}$ alkyl group (e.g. methyl, ethyl, isopropyl, trifluoromethyl, etc.) or an optionally halogenated $C_{1-4}$ alkoxy group (e.g. methoxy, ethoxy, isorpropoxy, trifluoromethoxy, etc.). More preferably, the ring B includes, for example, an optionally substituted benzene ring of the above formula [B] wherein (1) $B^1$, $B^2$ and $B^3$ are all hydrogen atom, (2) $B^1$ is a halogen atom, an optionally halogenated $C_{1-4}$ alkyl group or an optionally halogenated $C_{1-4}$ alkoxy group, and, $B^2$ and $B^3$ are both hydrogen, (3) $B^1$ is a hydrogen atom, and, $B^2$ and $B^3$ independently stand for an optionally halogenated $C_{1-4}$ alkoxy group, or (4) $B^1$, $B^2$ and $B^3$ independently stand for an optionally halogenated $C_{1-4}$ alkoxy group, (5) $B^1$ is an optionally halogenated $C_{1-4}$ alkyl group, and, $B^2$ and $B^3$ are both hydrogen, or (6) $B^1$ is an optionally halogenated $C_{1-4}$ alkoxy group, and $B^2$ and $B^3$ are both hydrogen.

Concrete examples of the atoms and groups in the above items (1) to (6) have the same meanings as defined hereinabove.

As more preferable ring B or ring B' substituents, use is made of, for example, an optionally substituted benzene ring of the above formula [B] wherein (a) $B^1$, $B^2$ and $B^3$ are all hydrogen, (b) $B^1$ is chlorine, fluorine, methyl, trifluoromethyl or methoxy, and, $B^2$ and $B^3$ are both hydrogen, (c) $B^1$ is hydrogen, and, $B^2$ and $B^3$ are both methoxy, or (d) $B^1$, $B^2$ and $B^3$ are all methoxy group, (e) $B^1$ is methyl group, $B^2$ and $B^3$ are both hydrogen, or (f) $B^1$ is methoxy group, $B^2$ and $B^3$ are both hydrogen.

As preferable ring C or ring C' substituents, use is made of, for example, a benzene ring optionally substituted with one to four, preferably two or three substituents selected from a halogen atom (e.g. fluorine, chlorine, bromine, etc.), an optionally halogenated $C_{1-4}$ alkyl group (e.g. methyl, ethyl, isopropyl, trifluoromethyl etc.), an optionally halogenated $C_{1-4}$ alkoxy group (e.g. methoxy, ethoxy, isopropoxy, trifluoromethoxy etc.), a mono- or di-$C_{1-4}$ alkylamino group (e.g. methylamino, dimethylamino, etc.), an amino group, a $C_{1-3}$ acyloxy group (e.g. acetoxy, etc.), a carboxyl group or a hydroxyl group. The ring C includes preferably, for example, an optionally substituted benzene ring represented by the formula [C]:

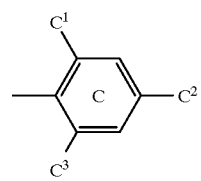

wherein $C^1$, $C^2$ and $C^3$ independently stand for a hydrogen atom, a halogen atom (e.g. fluorine, chlorine, etc.), an optionally halogenated $C_{1-4}$ alkyl group (e.g. methyl, ethyl, isopropyl, trifluoromethyl etc.), an optionally halogenated $C_{1-4}$ alkoxy group (e.g. methoxy, ethoxy, isopropoxy, trifluoromethoxy etc.) or a di-$C_{1-4}$ alkylamino group (e.g. dimethylamino, etc.) or the formula [C']:

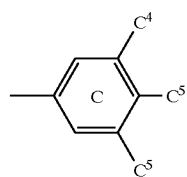

wherein $C^4$, $C^5$ and $C^6$ independently stand for a hydrogen atom, an optionally halogenated $C_{1-4}$ alkyl group (e.g. methyl, ethyl, isopropyl, t-butyl, trifluoromethyl, etc.), an optionally halogenated $C_{1-4}$ alkoxy group (e.g. methoxy, ethoxy, isopropoxy, trifluoromethoxy, etc.), a $C_{1-3}$ acyloxy group (e.g. acetoxy, etc.) or a hydroxyl group. More preferably, the ring C includes a substituted benzene ring represented by the above-mentioned [C] or [C'], wherein (1) $C^1$, $C^2$ and $C^3$ independently stand for a halogen atom, an optionally halogenated $C_{1-4}$ alkyl group or an optionally halogenated $C_{1-4}$ alkoxy group, (2) $C^1$ and $C^2$ independently stand for a halogen atom, an optionally halogenated $C_{1-4}$ alkyl group or an optionally halogenated $C_{1-4}$ alkoxy group, and $C^3$ is hydrogen, (3) $C^1$ and $C^3$ independently stand for a halogen atom, an optionally halogenated $C_{1-4}$ alkyl group or an optionally halogenated $C_{1-4}$ alkoxy group, and $C^2$ stands for a hydrogen atom, (4) $C^1$ and $C^3$ are a hydrogen atom, and $C^2$ is a halogen atom, (5) $C^1$ and $C^2$ stand for a hydrogen atom, and $C^3$ stands for a halogen atom or an optionally halogenated $C_{1-4}$ alkoxy group, (6) $C^1$ and $C^3$ stand for a hydrogen atom, and $C^2$ stands for an optionally halogenated $C_{1-4}$ alkoxy group, (7) $C^1$ and $C^3$ stand for a hydrogen atom, and $C^2$ stands for a di-$C_{1-4}$ alkylamino group, (8) $C^4$, $C^5$ and $C^6$ independently stand for a hydrogen atom, an optionally halogenated $C_{1-4}$ alkyl group or an optionally halogenated $C_{1-4}$ alkoxy group, (9) $C^4$ stands for an optionally halogenated $C_{1-4}$ alkyl group, $C^5$ and $C^6$ stand for a hydrogen atom, or

(10) $C^4$ and $C^6$ independently stand for an optionally halogenated $C_{1-4}$ alkyl group, and $C^5$ stands for a hydrogen atom.

Concrete examples of the atoms and groups in the above items (1) to (10) have the same meanings as defined hereinabove.

As more preferable optionally substituted benzene rings of ring C or ring C', use is made of those represented by the formula [C] or [C'], wherein (a) $C^1$, $C^2$ and $C^3$ independently are a fluorine, chlorine, methyl, trifluoromethyl, isopropyl, methoxy or ethoxy group, (b) $C^1$ and $C^2$ independently are a fluorine, chlorine, isopropyl, trifluoromethyl, methoxy, ethoxy or isopropoxy group, and $C^3$ is a hydrogen atom, (c) $C^1$ and $C^3$ independently are a fluorine, chlorine, methyl, trifluoromethyl, ethyl, isopropyl, methoxy, ethoxy or isopropoxy group, and $C^2$ is a hydrogen atom, (d) $C^2$ is a fluorine or chlorine, and $C^1$ and $C^3$ are a hydrogen atom, (e) $C^1$ and $C^3$ are a hydrogen atom, and $C^3$ is a fluorine, chlorine or methoxy group, (f) $C^1$ and $C^3$ are a hydrogen atom, and $C^2$ is a methoxy or isopropoxy group, (g) $C^1$ and $C^3$ are a hydrogen atom, and $C^2$ is a N,N-dimethylamino group, (h) $C^4$, $C^5$ and $C^6$ independently are a fluorine, chlorine, methyl, ethyl, isopropyl, trifluoromethyl, methoxy, ethoxy or isopropoxy group, (i) $C^4$ is a methyl, ethyl, isopropyl or trifluoromethyl group, and $C^5$ and $C^6$ are a hydrogen atom, or (j) $C^4$ and $C^6$ independently are a methyl, ethyl, isopropyl, trifluoromethyl, and $C^5$ is a hydrogen atom.

X stands for —NR—, wherein R is a hydrogen atom or an optionally substituted hydrocarbon group, —O— or —S—. Preferable examples of X are —NR— or —O—.

In the above-mentioned formulae, R and $R^a$ stand for hydrogen atom or an optionally substituted hydrocarbon group. As the hydrocarbon group, use is made of, for example, alkyl group, alkenyl group, alkynyl group, cycloalkyl group, aryl group, etc., preferably alkyl group.

As the alkyl group, use is made of a straight-chain or branched $C_{1-6}$ alkyl group such as methyl, ethyl, propyl, isopropyl, butyl, isobutyl, sec-butyl, tert-butyl, pentyl, hexyl. Preferably, a straight-chain or branched $C_{1-4}$ alkyl group such as methyl, ethyl, propyl, isopropyl, butyl.

As the alkenyl group, use is made of a $C_{2-6}$ alkenyl group such as ethenyl, propenyl, isopropenyl, butenyl, isobutenyl, sec-butenyl or the like, preferably a $C_{2-4}$ alkenyl group such as ethenyl, propenyl, isopropenyl or the like.

As the alkynyl group, use is made of a $C_{2-6}$ alkynyl group such as ethynyl, propynyl, isopropynyl, butynyl, isobutynyl, sec-butynyl or the like, preferably a $C_{2-4}$ alkynyl group such as ethynyl, propynyl, isopropynyl or the like.

As the cycloalkyl group, use is made of a $C_{3-8}$ cycloalkyl group such as cyclopropyl, cyclobutyl, cyclopentyl, cyclohexyl or the like, preferably a $C_{3-6}$ cycloalkyl group such as cyclopropyl, cyclobutyl or the like.

As the aryl group, use is made of a $C_{6-14}$ aryl group such as phenyl, naphthyl, anthryl, phenanthryl or the like, preferably a $C_{6-10}$ aryl group such as phenyl, naphthyl or the like.

As substituents of the optionally substituted hydrocarbon group, use is made of, for example, (i) halogen, (ii) cycloalkyl group, (iii) aryl group, (iv) amino group optionally substituted with alkyl, alkenyl, cycloalkyl or aryl, (v) hydroxyl group, (vi) optionally halogenated alkoxy group, (vii) acyl group, (viii) acyloxy group, (ix) cyano group, (x) optionally protected carboxyl group, (xi) carbamoyl group, (xii) mercapto group, (xiii) alkylthio group, (xiv) sulfo group and (xv) alkylsulfonyl group.

The optionally substituted hydrocarbon group may be substituted with one to four, preferably one or two, of these substituents which may be the same or different.

Referring to these substituents of hydrocarbon group, as the halogen atom, use is made of, for example, fluorine, chlorine, bromine and iodine, preferably fluorine and chlorine. As the cycloalkyl group, use is made of, for example, a $C_{3-6}$ cycloalkyl group such as cyclopropyl, cyclobutyl, cyclopentyl or cyclohexyl. As the aryl group, use is made of, for example, a $C_{6-10}$ aryl group such as phenyl or naphthyl. In the amino group optionally substituted with one or two alkyl, alkenyl, cycloalkyl or aryl groups, as the alkyl group, use is made of, for example, a $C_{1-4}$ alkyl group such as methyl, ethyl, propyl and isopropyl; as the alkenyl group, use is made of, for example, a $C_{2-4}$ alkenyl group such as ethenyl, propenyl, isopropenyl and butenyl; as the cycloalkyl group, use is made of, for example, a $C_{3-6}$ cycloalkyl group such as cyclopropyl, cyclobutyl, cyclopentyl and cyclohexyl; and as the aryl group, use is made of, for example, a $C_{6-10}$ aryl group such as phenyl and naphthyl. Preferable examples include an amino group and mono- or di-$C_{1-4}$ alkyl group, e.g. methylamino, dimethylamino or diethylamino. As the optionally halogenated alkoxy group, use is made of, for example, a $C_{1-4}$ alkoxy group such as methoxy, difluoromethoxy, trifluoromethoxy, ethoxy, 2,2,2-trifluorobutoxy, propoxy, isopropoxy, butoxy, 4,4,4-trifluorobutoxy, isobutoxy and sec-butoxy, or these groups on which one to three halogen atoms (e.g. fluorine, chlorine) are substituted. As the acyl group, use is made of a $C_{1-4}$ acyl group such as formyl, acetyl, propionyl, butyryl and isobutyryl. As the acyloxy group, use is made of a $C_{1-4}$ acyloxy group such as formyloxy, acetyloxy, propionyloxy, butyryloxy and isobutyryloxy. As the protecting group of the optionally protected carboxyl group, use is made of, for example, a $C_{1-4}$ alkyl group such as methyl, ethyl and t-butyl group, and a $C_{7-11}$ aralkyl group such as benzyl. The preferable examples of the optionally protected carboxyl group include a carboxyl group or a $C_{1-4}$ alkoxy-carbonyl group (e.g. methoxycarbonyl, ethoxycarbonyl, etc.) As the alkylthio group, use is made of, for example, a $C_{1-4}$ alkylthio group such as methylthio, ethylthio, propylthio, isopropylthio and butylthio. As the alkylsulfonyl group, use is made of, for example, a $C_{1-4}$ alkylsulfonyl group such as methylsulfonyl, ethylsulfonyl, propylsulfonyl, isopropylsulfonyl and butylsulfonyl.

Preferable examples of the substituent in the optionally substituted hydrocarbon group include (i) halogen, (ii) cycloalkyl group, (iii) aryl group, (iv) amino group optionally substituted with alkyl, alkenyl, cycloalkyl or aryl group, (v) hydroxyl group, (vi) optionally halogenated alkoxy group, (vii) acyl group, (viii) acyloxy group, (ix) cyano group, (x) optionally protected carboxyl group and (xi) carbamoyl group, more preferably, for example, (a) a $C_{3-6}$ cycloalkyl group, (b) a $C_{6-10}$ aryl group, (c) mono- or di-$C_{1-4}$ alkylamino group and (d) $C_{1-4}$ alkyl-carboxyl group.

Preferable examples of R and $R^a$ include (i) a hydrogen atom or (ii) a $C_{1-6}$ alkyl or $C_{3-8}$ cycloalkyl group which may be substituted with a substituent selected from the group consisting of a $C_{3-6}$ cycloalkyl a $C_{6-10}$ aryl, a mono- or di-$C_{1-4}$ alkylamino, a hydroxyl, and an optionally protected carboxyl, more preferable examples include hydrogen atom, methyl, ethyl, propyl, isopropyl, butyl, sec-butyl, tert-butyl, cyclopropyl, cyclopropylmethyl, benzyl, 2,2-dimethylaminoethyl, 2,2-diethylaminoethyl, 2-hydroxyethyl, carboxymethyl, methoxycarbonylmethyl, ethoxycarbonyl and t-butoxycarbonylmethyl.

Especially preferable examples of R and $R^a$ include hydrogen atom and a $C_{1-4}$ alkyl group (e.g., methyl, ethyl, propyl, isopropyl, etc.), more preferably, R is a $C_{1-4}$ alkyl group such as methyl, ethyl, propyl and isopropyl group and $R^a$ is a hydrogen atom.

In the above-mentioned formula, m denotes 0 or 1, preferably 0.

In the above-mentioned formula, n denotes 1 or 2, especially preferably 1.

Preferable examples of each symbols in the formula (I) and (I'') are the follow:

(1)—i ring A is a benzene ring which may be substituted with one or two substituents selected from the group consisting of a halogen atom (e.g., fluorine, chlorine, bromine, etc.) and an optionally halogenated $C_{1-4}$ alkyl group (e.g., methyl, ethyl, isopropyl, trifluoromethyl, etc.), (1)—ii ring A is a group of the formula:

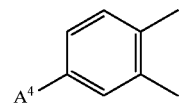

wherein $A^4$ is a halogen atom (e.g., fluorine, chlorine, etc.)

(2)—i ring B and B' is a benzene ring which may be substituted with one or two substituents selected from the group consisting of an optionally halogenated $C_{1-4}$ alkyl group (e.g., methyl, ethyl, isopropyl, trifluoromethyl, etc.) and an optionally halogenated $C_{1-4}$ alkoxy group (e.g., methoxy, ethoxy, isopropoxy, trifluoromethoxy, etc.), (2)—ii ring B and B' is a group of the formula:

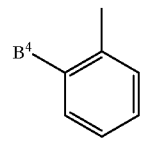

wherein $B^4$ is an optionally halogenated $C_{1-4}$ alkyl group (e.g., methyl, ethyl, isopropyl, trifluoromethyl etc.) or a $C_{1-4}$ alkoxy group (e.g., methoxy, ethoxy, isopropoxy, etc.), (3)—i ring C and C' is a benzene ring which may be substituted with one to three substituents selected from the group consisting of a halogen atom (e.g., fluorine, chlorine, etc.), an optionally halogenated $C_{1-4}$ alkyl group (e.g., methyl, ethyl, isopropyl, trifluoromethyl, etc.) and an optionally halogenated $C_{1-4}$ alkoxy group (e.g., methoxy, ethoxy, isopropoxy, trifluoromethoxy, etc.), (3)—ii ring C and C' is a group of the formula:

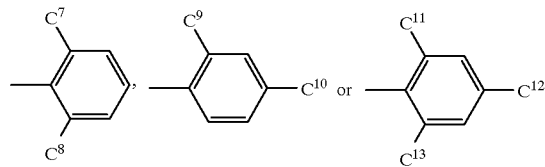

wherein $C^7$ and $C^8$ independently stand for a $C_{1-4}$ alkyl group (e.g., methyl, ethyl, isopropyl, etc.) or a $C_{1-4}$ alkoxy group (e.g., methoxy, ethoxy, isopropoxy, etc.); $C^9$ and $C^{10}$ independently stand for a halogen atom (e.g., fluorine, chlorine, etc.); $C^{11}$, $C^{12}$ and $C^{13}$ independently stand for a halogen atom (e.g., fluorine, chlorine, etc.) or a $C_{1-4}$ alkyl group (e.g., methyl, ethyl, isopropyl, etc.).

(4)—i X is —NR'— wherein R' is a $C_{1-4}$ alkyl group (e.g., methyl, ethyl, isopropyl, etc.) or —O—, (4)—ii X is —NR'— wherein R' is a $C_{1-4}$ alkyl group (e.g., methyl, ethyl, isopropyl, etc.), (4)—iii X is —O—, (5)—i Y is —$CH_2$—, —$CH_2CH_2$— or —NH—, (5)—ii Y is —$CH_2$—, (5)—iii Y is —NH—, (6)—i $R^a$ is a hydrogen.

Preferable combination:

|   | ring A | ring B and B' | ring C and C' | X | Y | R$^a$ |
|---|---|---|---|---|---|---|
| 1 | (1)-i | (2)-i | (3)-i | (4)-i | (5)-i | (6)-i |
| 2 | (1)-ii | (2)-ii | (3)-ii | (4)-ii | (5)-ii | (6)-i |
| 3 | (1)-ii | (2)-ii | (3)-ii | (4)-iii | (5)-ii | (6)-i |
| 4 | (1)-ii | (2)-ii | (3)-ii | (4)-iii | (5)-iii | (6)-i |

A condensed 5-membered cyclic compound shown by the formula (I") or a salt thereof can be produced by the following methods 1 or 2. Namely, 1: Carboxylic acid represented by the general formula (II) or a salt thereof or a reaction derivative thereof is allowed to react with amine represented by the general formula (III) or a salt thereof to produce the compound (I") or a salt thereof.

2: Amine represented by the general formula (IV) or a salt thereof is allowed to react with a compound represented by the general formula (V) or a salt thereof to produce the compound (I') or a salt thereof.

The above methods 1 and 2 are described in detail as follows:

Method 1: Reaction of the carboxylic acid represented by the general formula (II) or a salt thereof or a reaction derivative thereof with the compound (III) or a salt thereof is a reaction of forming amide linkage or urea linkage, which is conducted in various methods. For example, reaction of the compound (II) or a salt thereof (e.g. a salt of an alkali metal or alkaline earth metal such as sodium, potassium or magnesium) with the compound (III) or a salt thereof (e.g. a salt with an inorganic acid such as hydrochloric acid and sulfuric acid or a salt with an organic acid such as methanesulfonic acid, benzenesulfonic acid, toluenesulfonic acid, oxalic acid, fumaric acid and maleic acid) is, usually, preferably conducted by using a suitable condensing agent, or it is preferable to conduct the reaction after the compound (II) or a salt thereof is once led to a reactive derivative. As the condensing agent, use is made of, for example, dicyclohexylcarbodiimide, 1-(3-dimethylaminopropyl)-3-ethylcarbodiimide hydrochloride, diethyl cyanophosphate and diphenylphosphoryl azide. In the case of using a condensing agent exemplified as above, it is preferable, generally, to conduct the reaction in a solvent (e.g. ethers such as tetrahydrofuran, dioxane, dimethoxyethane, ethyl acetate, dichloromethane, 1,2-dichloroethane, benzene, toluene, N,N-dimethylformamide and dimethyl sulfoxide, esters, halogenated hydrocarbons, hydrocarbons, amides, sulfoxides, etc.). This reaction may be accelerated by allowing a base to exist and is conducted at about −10° C. to 100° C., preferably about 0° C. to 60° C. The reaction time ranges usually from 1 to 96 hours, preferably from 1 to 72 hours. The amounts of (III) or a salt thereof and the condensing agent are, relative to one mole of (II) or a salt thereof, 1 to 5 molar equivalents, preferably 1 to 3 molar equivalents, respectively. As the base, use is made of, for example, alkylamines such as triethylamine, cyclic amines such as N-methylmorpholine and pyridine. The amount of the base is, relative to 1 mole of (II) or a salt thereof, 1 to 5 molar equivalents, preferably 1 to 3 molar equivalents.

Examples of the reactive derivatives of (II) include acid halides (e.g. chloride, bromide, etc.), acid anhydrides, mixed acid anhydrides (e.g. anhydride with methyl carbonate, anhydride with ethyl carbonate, anhydride with isobutyl carbonate, etc.), active esters (e.g. ester with hydroxysuccinic acid imide, ester with 1-hydroxybenzotriazole, ester with N-hydroxy-5-norbornene-2,3-carboxyimide, ester with p-nitrophenol, ester with 8-oxyquinoline, etc.). The reaction of the compound (III) or a salt thereof with a reactive derivative of (II) is usually conducted in a solvent (e.g. halogenated hydrocarbons such as chloroform, dichloromethane, 1,2-dichloroethane, ethyl ether, tetrahydrofuran, dioxane, dimethoxyethane, ethyl acetate, benzene, toluene, pyridine and N,N-dimethylformamide, ethers, esters, hydrocarbons, amides). This reaction may be accelerated by allowing a base to exist in the reaction system. The reaction temperatures ranges usually from about −10° C. to 120° C., preferably from about 0° C. to 100° C. The reaction time ranges usually from 1 to 48 hours, preferably from 1 to 24 hours. The amount of (III) or a salt thereof ranges, relative to one mole of the reactive derivative of (II), from 1 to 5 molar equivalents, preferably from 1 to 3 molar equivalents. As the base, use is made of, for example, alkyl amines such as triethylamine, etc., cyclic amines such as N-methylmorpholine, pyridine, etc., aromatic amine such as N,N-dimethylaniline, N,N-diethylaniline, etc., alkali metal carbonates such as sodium carbonate, potassium carbonate, etc., and alkali metal hydrogencarbonates such as sodium hydrogencarbonate, potassium hydrogencarbonate, etc., and the amount of the base ranges, relative to 1 mole of (II) or a reactive derivative thereof, from 1 to 5 molar equivalents, preferably from 1 to 3 molar equivalents. And, when a solvent immiscible with water is used in this reaction, the reaction may be allowed to proceed in a two-phase system by the addition of water. Further, in the method 1 above, when Y in the compound (II) stands for —NH— or —CH$_2$NH—, as a reactive derivative thereof, use is preferably made of corresponding isocyanates [(II-2), (II-3) to be described later]. Reaction of these isocyanates with the compound (III) or a salt thereof produces a urea derivative. In this reaction, while the compound (III) itself may be used as the solvent, the reaction may be conducted in another solvent which does not interfere with the proceeding of the reaction, as exemplified by, preferably, ethers (e.g. diethyl ether, diisopropyl ether, tetrahydrofuran, dioxane, dimethoxyethane, etc.), aromatic hydrocarbons (e.g. benzene, toluene, xylene, etc.), esters (e.g. methyl acetate, ethyl acetate, etc.), amides (e.g. N,N-dimethylformamide, etc.), sulfoxides (e.g. dimethyl sulfoxide, etc.). In the case where the compound (III) is used in the form of a salt, the reaction can be allowed to proceed significantly by, upon necessity, the addition of a desalting agent. In this case, as the desalting agent, use is preferably made of, for example, tertiary amines such as trimethylamine, triethylamine, N-methylmorpholine, etc., and aromatic amines such as pyridine, picoline, N,N-dimethylaniline, etc., among others. The amount of these desalting agents to be employed ranges from 1 to 5 molar equivalent, preferably 1 to 3 molar equivalents, relative to 1 mole of the salt of (III) then employed. The reaction temperature ranges from −10° C. to 180° C., preferably from 0° C. to 120° C. The reaction time ranges usually from 15 minutes to 40 hours, preferably from 30 minutes to 20 hours. The amount of (III) or a salt thereof to be employed ranges from 1 to 5 molar equivalents, preferably 1 to 3 molar equivalents.

Method 2: This is a method of producing a urea derivative by allowing the compound (IV), i.e. an amine derivative, or a salt thereof (e.g. a salt with a mineral acid such as hydrochloric acid, sulfuric acid, etc., or a salt with an organic acid such as toluenesulfonic acid, oxalic acid fumaric acid or maleic acid) to react with the compound (V), i.e. an isocyanate derivative. This method can be conducted in the same manner as in the above-mentioned reaction of (II-2), (II-3) with (III).

In case when the compound (I") or a salt thereof produced by the above-mentioned method 1 or 2 contains a lower alkoxy group in the benzene ring in ring A, ring B', ring C' and a group shown by R and R$^a$, this lower alkoxy group, when necessary, can be converted to hydroxyl group by allowing it to react with, for example, boron tribromide. This reaction is usually conducted in a solvent (e.g. halogenated hydrocarbons such as dichloromethane, chloroform, carbon tetrachloride, benzene, toluene, etc. and hydrocarbons) at temperatures ranging from about −20° C. to 80° C., preferably from about 0° C. to 30° C. The amount of boron tribromide to be employed ranges from about 1 to 10 molar equivalents, preferably from about 1 to 5 molar equivalents, relative to one lower alkoxy group. The reaction time ranges usually from 15 minutes to 24 hours, preferably from 30 minutes to 12 hours. And, in case when the compound (I") or a salt thereof produced by the above-mentioned method 1 or 2 contains hydroxyl group in ring A, ring B', ring C' and a group shown by R and $R^a$, this hydroxyl group, when necessary, can be converted to alkoxy group or acyloxy group by subjecting it to alkylation or acylation. The alkylation is conducted by using an alkylating agent such as an optionally substituted alkane halide (e.g. chloride, bromide, iodide, etc.), sulfuric acid ester or sulfonic acid ester (e.g. methane sulfonate, p-toluenesulfonate, benzene sulfonate, etc.) in a solvent (e.g. alcohols such as methanol, ethanol, propanol, etc., ethers such as dimethoxyethane, dioxane, tetrahydrofuran, etc., ketones such as acetone, amides such as N,N-dimethylformamide, etc.) in the presence of a base (e.g. an organic base such as trimethylamine, triethylamine, N-methyl morpholine, pyridine, picoline, N,N-dimethylaniline, etc. and an inorganic base such as potassium carbonate, sodium carbonate, potassium hydroxide, sodium hydroxide, etc.). The reaction temperatures range usually from −10° C. to 100° C., preferably from about 0° C. to 80° C. The amount of these alkylating agents to be used ranges from about 1 to 5 molar equivalents, preferably about 1 to 3 molar equivalents, relative to one mole of the starting phenolic derivative. The reaction time ranges usually from 15 minutes to 24 hours, preferably 30 minutes to 12 hours.

The acylation is conducted by using a desired carboxylic acid or as reactive derivative thereof. This reaction is conducted, while depending on the kinds of the acylating agent and of the starting phenolic derivative, usually in a solvent (e.g. hydrocarbons such as benzene, toluene, ethyl ether, ethyl acetate, chloroform, dichloromethane, dioxane, tetrahydrofuran, N,N-dimethylformamide, pyridine, etc., ethers, esters, halogenated hydrocarbons, amides, aromatic amines, etc.), and, for accelerating the reaction, a suitable base (e.g. hydrogen carbonates such as sodium hydrogencarbonate, potassium hydrogencarbonate, etc., carbonates such as sodium carbonate, potassium carbonate, etc., acetates such as sodium acetate, etc., tertiary amines such as triethylamine, etc., aromatic amines such as pyridine, etc.) can be added to the reaction system. As reactive derivatives of carboxylic acid, use is made of acid anhydrides, mixed acid anhydrides, acid halides (e.g. chloride, bromide), etc. The amount of these acylating agent to be used ranges from 1 to 5 molar equivalents, preferably 1 to 3 molar equivalents, relative to one mole of the starting phenolic derivative. The reaction temperatures ranges usually from 0° C. to 150° C., preferably from about 10° C. to 100° C. The reaction time ranges usually from 15 minutes to 12 hours, preferably, from 30 minutes to 6 hours.

By the methods described above, when the compound (I") is obtained in the free state, it can be made, in accordance with a conventional process, into a salt with an organic acid (e.g. methanesulfonic acid, benzenesulfonic acid, oxalic acid, fumaric acid, maleic acid, tartaric acid, etc.), and, when the compound (I") is obtained as the corresponding salt, it can be converted, in accordance with a conventional process, into the free form or any other salt.

The object compound (I") or a salt thereof obtained by the methods described above can be purified and recovered by using a per se conventional separation and purification means (e.g. concentration, solvent extraction, column chromatography, recrystallization or the like).

The starting compounds (II) and (IV) or salts of them can be produced, with an industrial advantage, by the method shown in the following schema or methods analogous thereto.

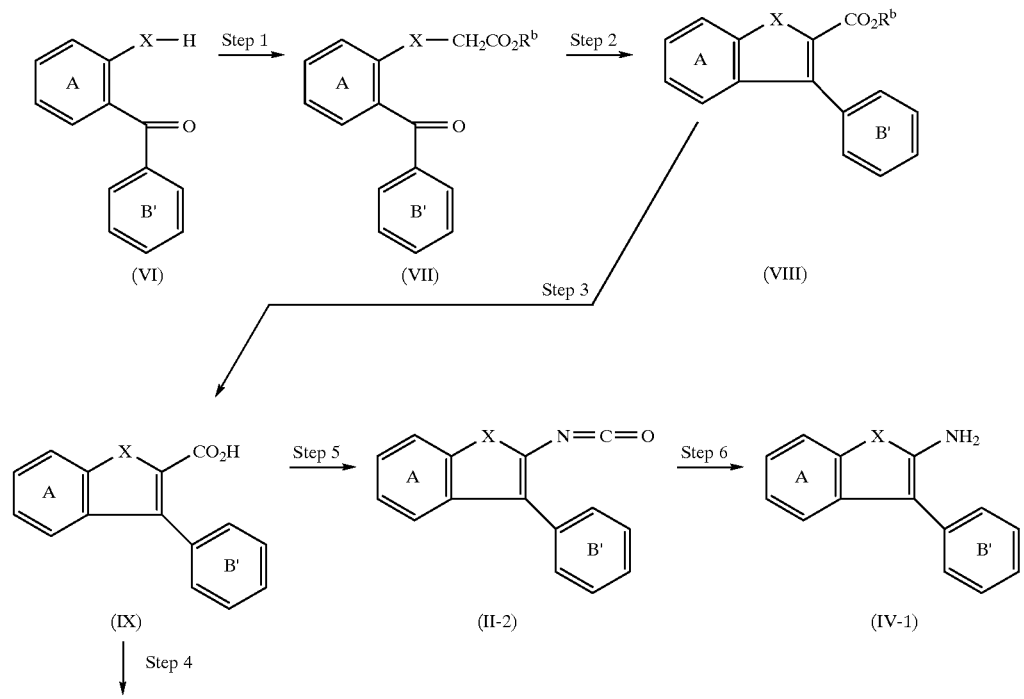

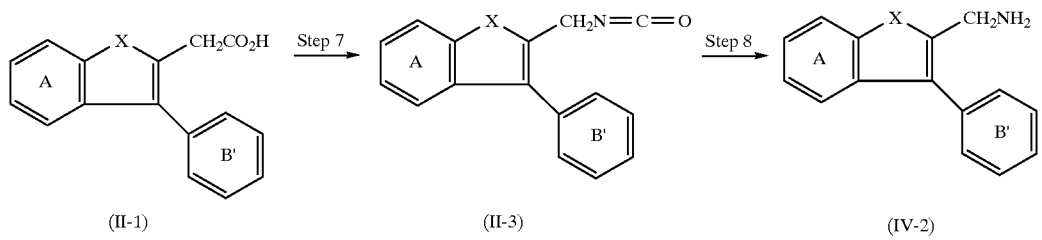

wherein $R^b$ stands for a carboxyl-protecting group, and other symbols are of the same meaning as defined above.

Among the compounds (IX) and (II-1), those wherein X is —O— can be produced from the compound (VI) (X=O) by the method (steps 1–4) disclosed by J. N. Chatterjea, et al. in Journal of Indian Chemical Society, 45, pp.171–177, 1968 or methods analogous thereto. Among the compounds (IX) and (II-1), those wherein X is —NR— and —S— can also be produced by substantially the same methods as mentioned above.

Further to state, among the compounds (II-1), those wherein X is —NR— can be produced also by a known method "U. M. Teotino et al., in Gazzetta Chimica Italiana, pp.1853–1862, 1959" employing phenyl hydrazines and γ-phenyl acetoacetic acid esters as the starting material.

Step 5 is to obtain (II-2) [this compound corresponds to the compound (II) wherein Y is —NH—] by converting carboxyl group of the compound (IX) to isocyanate, i.e. usually by leading (IX) to an acid azide derivative which is then converted to the corresponding isocyanate derivative. While various modifications of this method have been disclosed in literature references, any one of them can be applied to the method starting from the compound (IX).

For example, by allowing an azidating agent [e.g. diphenyl phosphoryl azide (hereinafter abbreviated as DPPA) to react with the compound (IX), an acid azide derivative of (IX) can be produced. This reaction can be conducted usually in a solvent inert to the reaction (e.g. ethers such as ethyl ether, isopropyl ether, dimethoxyethane, tetrahydrofuran, dioxane, etc., aromatic hydrocarbons such as benzene, toluene, xylene, etc., esters such as methyl acetate, ethyl acetate, etc., ketones such as acetone, 2-butanone, etc., aromatic amines such as pyridine, etc., amides such as N,N-dimethylformamide, etc.). It is also possible that this reaction can be accelerated by allowing the reaction to proceed in the presence of a base (e.g. trimethylamine, triethylamine, N-methyl morpholine, etc.). The reaction time ranges usually from about 5 minutes to 12 hours, preferably from about 10 minutes to 6 hours. The reaction temperature ranges usually from about –10° C. to 150° C., preferably from about –5° C. to 120° C. The amount of an azidating agent (e.g. DPPA or the like) to be employed ranges from 1 to 3 molar equivalents, preferably from 1 to 2 molar equivalents.

While the resultant acid azide can be isolated and refined by a per se known method, it is converted to the isocyanate compound (II-2) by usually heating the reaction mixture as it is without isolating the acid azide. This conversion reaction is conducted preferably by using the same solvent as employed for the azidation at temperatures ranging usually from about 20° C. to 200° C., preferably from about 30° C. to 150° C. The reaction time ranges usually from about 5 minutes to 10 hours, preferably from about 5 minutes to 6 hours. The compound (II-2) thus obtained is isolated by a per se conventional means, or, without isolating from the reaction mixture, it can be used as the starting compound for producing the compound (I") or (I') wherein Y stands for —NH—.

Step 7 is to convert the acetic acid derivative (II-1) into the isocyanate compound (II-3). This step can be carried out substantially in accordance with the manner described in Step 5.

Step 6 and Step 8 are to convert the isocyanate group of (II-2) and (II-3) into amino group to obtain (IV-1) and (IV-2) respectively. The reaction is conducted usually under hydrolytic conditions. This reaction is conducted, for example, in a solvent (e.g. alcohols such as methanol, ethanol, propanol, butanol, etc., ethers such as tetrahydrofuran, dioxane, dimethoxyethane, etc., or mixture solvents of them, etc.) under alkaline conditions using, for example, alkali or alkaline earth metal hydroxide such as sodium hydroxide, barium hydroxide or the like, or under acid conditions using, for example, an inorganic acid such as hydrochloric acid, bromic acid, sulfuric acid or the like. The reaction temperature ranges usually from about 0° C. to 120° C., preferably from about a 5° C. to 100° C. The reaction time ranges from about 30 minutes to 36 hours, preferably from about one hour to 20 hours.

And, among compounds of (IV-1), those in which X stands for —NR—, can also be produced by a known method "e.g. G. Winters, et al., Farmaco, Edizione Scientifica, 34, pp. 507–517 (1979)" or a method analogous thereto.

The compound (I) described in EP-A1-512570 can be advantageously produced by using the compound (IV-2) in the present invention.

In the above-mentioned methods, when a starting compound containing, as a substituent, a reactive group such as amino group, hydroxyl group, carboxyl or the like, is employed, the substituent may, upon necessity, be protected by a conventional method. Thus introduced protecting group may, upon necessity, be removed by subjecting the reaction product to conventional deprotection reaction to thereby obtain the object compound (I), (I'), (I") or an intermediate for producing them or a salt thereof.

As such protecting groups as above, use is conveniently made of, for example, those employed in the field of peptide chemistry. Among them, as amino-protecting groups, use is preferably made of, for example, formyl, chloroacetyl, tertiary butoxy carbonyl, benzyloxy carbonyl, p-methoxy benzyloxy carbonyl, 2-trimethyl silyl ethoxy carbonyl, 2,2,2-trichloroethoxy carbonyl, trityl, etc. As hydroxyl-protecting groups, use is made of, for example, chloroacetyl, benzyl, p-nitrobenzyl, methyl thiomethyl, methoxy methyl, trimethyl silyl, tertiary butyl dimethyl silyl, 2-tetrahydropyranyl, 4-methoxy-4-tetrahydropyranyl, p-nitrobenzyloxy carbonyl, allyloxy carbonyl, etc. As carboxyl-protecting groups, use is made of, for example, benzyl, benzhydryl, trityl, p-methoxybenzyl, p-nitrobenzyl, tertiary butyl, allyl, etc.

In the above-mentioned methods, when the starting compounds or intermediates for synthesizing them contain amino group or carboxyl group or the like, they can be made into salts, by a conventional method, with, for example, an inorganic acid (e.g. hydrochloric acid, sulfuric acid, hydrobromic acid, etc.), an organic acid (e.g. methanesulfonic acid, benzenesulfonic acid, toluenesulfonic acid, oxalic acid, fumaric acid, maleic acid, tartaric acid, etc.), an inorganic base (e.g. alkali metal such as sodium, potassium, etc., alkaline earth metal such as calcium, magnesium, etc., aluminum or ammonium, etc.) or an organic base (e.g. trimethylamine, triethylamine, pyridine, picoline, ethanolamine, diethanolamine, triethanolamine, dicyclohexylamine or N,N'-dibenzylethylenediamine, etc.), upon necessity.

The compound obtained in each of the above-mentioned steps can be purified or recovered by a per se known refining means such as concentration, pH change, phasic transfer, solvent extraction, column chromatography, crystallization, recrystallization or the like, or it may be used in the subsequent reaction step, respectively, in the state of reaction mixture.

The compounds (I), (I") or their pharmaceutically acceptable salts (e.g. above-mentioned salts with inorganic or organic bases, or salts with inorganic or organic acids) have an excellent acyl-CoA:cholesterol acyltransferase (ACAT) inhibitory action, and they are low in acute toxicity and toxicity due to continuous administration, thus being administered safely as medicines. ACAT has been known that it is an enzyme taking part in converting intracellular cholesterol into higher fatty acid ester and that it takes an important role for absorbing intestinal cholesterol as ester and for accumulation of cholesterol in peripheral organs, cells (e.g. arterial wall, macrophage or the like), etc. as ester. Therefore, substances having the ACAT inhibitory action inhibit absorption of alimentary cholesterol from intestinal canal, control the increase of blood cholesterol and, at the same time, suppress the accumulation of intracellular cholesterol ester in the lesion of arteriosclerosis and prevent the development of atherosis. Therefore, the compounds (I), (I") or their salts of this invention are useful as safely administrable prophylactic and therapeutic agents against hypercholesterolemia, atherosclerosis and diseases caused by them (e.g. ischemic heart diseases such as myocardial infarction, etc., cerebral blood vessel disorders such as cerebral infarction, cerebral apoplexy, etc.) in mammals (e.g. mice, rats, hamsters, rabbits, cats, dogs, horses, cows, sheep, monkeys, man, etc.).

And, among the compounds (I), (I") or their salts, there are included compounds showing an action of controlling the formation of peroxide lipid (antioxidant action) (for example, the compounds (I) or (I"), wherein at least one of ring A, ring B and ring C is a benzene ring substituted with amino group or hydroxyl group optionally substituted with a $C_{1-4}$ alkyl group). It has been known that peroxidation of lipid in a living body is deeply concerned with occurrence of arteriosclerosis or cerebral and cardial ischemic diseases. Therefore, the compounds (I), (I") or their salts having both ACAT inhibitory action and antioxidant action serve to prophylaxis and therapy of various diseases of vessels caused by blood cholesterol and lipid peroxide, thus they are highly useful as medicines.

When the compounds represented by the general formula (I) or (I") or their pharmaceutically acceptable salts are used as the above-mentioned medicinal preparations, they are mixed with a suitable pharmacologically acceptable carrier, an excipient (e.g. starch, lactose, sucrose, calcium carbonate, calcium phosphate, etc.), a binding agent (e.g. starch, gum arabica, carboxymethyl cellulose, hydroxypropyl cellulose, crystalline cellulose, alginic acid, gelatin, polyvinyl pyrrolidone, etc.), a lubricant (e.g. stearic acid, magnesium stearate, calcium stearate, talc, etc.), a disintegrator (e.g. carboxymethyl cellulose calcium, talc, etc.), a diluent (e.g. physiological saline, etc.), etc., and prepared, by conventional means, into powders, fine granules, granules, tablets or injections, which can be administered orally or non-orally. When they are used for inhibiting absorption of cholesterol, oral administration is more preferable. While the daily dosage varies with the kinds of the compounds (I), (I") or their salts, administration route, symptoms, ages of patients or the like, it ranges, when orally administered to an adult patient of hypercholesterolemia, from about 0.005 to 5 mg, preferably from about 0.05 to 10 mg, more preferably, from about 0.2 to 4 mg per 1 kg of body weight, and this amount is preferably administered once daily or divided into three times daily.

[Action]

The compounds (I), (I") or their salts of this invention have an excellent ACAT inhibitory action, and their pharmacological test results are shown as follows.

(1) Acyl-CoA:cholesterol acyltransferase (ACAT) inhibitory action

[Method of experiment]

In accordance with the method disclosed by Heider et al. on Journal of Lipid Research, 24, p.1127 (1983), an enzyme sample ACAT was prepared from the microsomal fraction of mucosal cells from the small intestines of rats (6-week old male Sprague-Dawleys) fasted for 20 hours.

The ACAT activity was determined by, in accordance with the method disclosed by Helgerud et al. on Journal of Lipid Research 22, p.271 (1981), measuring the amount of labeled cholesterol ester from $[1-^{14}C]$oleoyl-CoA and endogenous cholesterol.

[Results]

(1) In Table 2, the labeled cholesterol ester formation inhibitory rate (%) determined when supplemented with $10^{-6}$M of a test compound (a representative one of the compounds obtained in the following Examples 1 to 24) is shown as the index of ACAT inhibitory activity.

TABLE 2

| Test Compound (Example No.) | ACAT inhibitory rate (%) $10^{-6}$M |
|---|---|
| 1 | 99.2 (93.7)* |
| 2 | 98.8 |
| 3 | 90.8 |
| 4 | 99.0 |
| 5 | 93.2 |
| 7 | 92.3 |
| 8 | 91.2 |
| 11 | 99.1 (92.2)* |
| 16 | 98.1 (50.3)* |
| 17 | 92.9 |
| 18 | 90.1 |
| 19 | 99.0 (28.8)* |
| 20 | 99.4 (39.9)* |

*In the parentheses is shown the inhibitory rate at $10^{-8}$M.

Table 2 shows that the compounds (I), (I") or salts thereof have excellent ACAT inhibitory activity.

(2) Hypocholesterolemic activity (Cholesterol-lowering activity)

[Method of experiment]

Groups of 6 ICR mice (2 subgroups of 3 mice) were made hypercholesterolemic by being fed a high cholesterol-cholic acid diet for 7 days and administered with test compounds orally on the last two days. One-half of the total dose was given on day 6 followed by the other half on day 7. After fasting overnight (16 hours after the last dose), the animals were sacrificed and sera were collected together for the each subgroup for measuring the levels of cholesterol and heparin precipitating lipoproteins (HPL). Both cholesterol and HPL levels were measured with autoanalyzer by the enzymatic CHOD-PAP method for the former and by the turbidimetric method of Shurr et. al. [in C. E. Dau ed. Atherosclerosis Drug Discovery, Plenum Publishing, New York, pp.215–229 & 231–249, 1976.] for the latter.

[Results]

Table 3 shows reduction % (compared to control groups) of cholesterol and HPL.

TABLE 3

| Test compounds | Dose (po) | Reduction % | |
|---|---|---|---|
| (Example No.) | mg/kg. | cholesterol | HPL |
| 1 | 30 | 32 | 27 |
| 11 | 10 | 31 | 38 |
| 11 | 1 | 28 | 27 |

From Table 3, it is clear that compounds (I), (I") or a salt thereof exhibits excellent hypocholesterolemic activity.

EXAMPLES

The present invention is hereinafter described in more detail by means of the following Examples and Reference Examples. The following Reference Examples and Examples are further descriptive of the present invention. It should be understood that these are merely illustrative and by no means definitive of the invention and that many changes and modifications can be made within the scope of the invention.

Elution in column chromatography in the Reference and Examples and Reference Examples were conducted with observation by TLC (Thin Layer Chromatography), unless otherwise stated. In the TLC observations, a TLC plate of Merck 60F$_{254}$ was used, in which the developing solvent was the same as the column chromatography eluent and the detector was a UV detector. Silica gel used for column chromatography was Merck Silica gel 60(70–230 mesh). Room temperature is generally defined to be between about 10° C. and 35° C.

Extracts were dried over sodium sulfate or magnesium sulfate.

The abbreviations in the Examples and Reference Examples are defined as follows: DMF for dimethylformamide, THF for tetrahydrofuran, DMSO for dimethyl sulfoxide, Hz for Herz, J for coupling constant, m for multiplet, q for quartet, t for triplet, d for doublet, s for single and b for broad.

Example 1

N-[2,6-Bis(1-methylethyl)phenyl]-5-chloro-3-(2-methylphenyl)-2-benzofuranacetamide To a solution of 5-chloro-3-(2-methylphenyl)benzofuran-2-acetic acid (3.00 g) in anhydrous THF (30 ml) were added oxalyl chloride (1.30 ml) and DMF (one drop), then the mixture was stirred for 0.5 hour. The solvent was distilled off, and the residue was dissolved in dichloromethane (10 ml). This solution was added to a solution of 2,6-diisopropylaniline (2.50 ml) and triethylamine (3.00 ml) in dichloromethane (30 ml), then the mixture was stirred for one hour at room temperature. The solvent was distilled off. To the residue was added ethyl acetate, which was washed with water, dilute hydrochloric acid, water, an aqueous solution of sodium hydrogencarbonate and water, successively, which was then dried, followed by distilling off the solvent to give the title compound as colorless crystals (1.86 g). m.p.260–261° C. (recrystallized from ethyl acetate-isopropyl ether).

NMR (200 MHz, CDCl$_3$) ppm: 1.11(6H,d,J=7.0 Hz), 1.12(6H,d,J=6.8 Hz), 2.22(3H,s), 2.96(2H,m), 3.79(1H,d,J=16 Hz), 3.89(1H,d,J=16 Hz), 6.90–7.50(11H,m)

Elemental Analysis for C$_{29}$H$_{30}$NO$_2$Cl: Calcd.: C, 75.72; H, 6.57; N, 3.04 Found: C, 75.71; H, 6.66; N, 3.17

In Examples 2 to 5, substantially the same reaction as in Example 1 was conducted, by employing benzofuran-2-acetic acid and aniline respectively corresponding to the respective title compounds as the starting materials, to obtain the objective compounds.

Example 2

5-Chloro-N-(2,6-dimethoxyphenyl)-3-(2-methylphenyl)-2-benzofuranacetamide m.p. 185–187° C. (recrystallized from ethyl acetate-isopropyl ether)

NMR (200 MHz, CDCl$_3$) ppm: 2.21(3H,s), 3.75(8H,s like), 6.54(2H,d,J=8.4 Hz), 6.81(1H,bs), 7.10–7.50(8H,m)

Elemental Analysis for C$_{25}$H$_{22}$NO$_4$Cl: Calcd.: C, 68.89; H, 5.09; N, 3.21 Found: C, 69.00; H, 5.35; N, 3.49

Example 3

5-Chloro-3-(2-methylphenyl)-N-(2,4,6-trimethylphenyl)-2-benzofuranacetamide m.p. 222–224° C. (recrystallized from ethyl ether-hexane)

NMR (200 MHz, CDCl$_3$) ppm: 2.10(6H,s), 2.21(3H,s), 2.24(3H,s), 3.81(2H,d,J=3.2 Hz), 6.86(2H,s), 6.95(1H,bs), 7.20–7.50(7H,m)

Elemental Analysis for C$_{26}$H$_{24}$NO$_2$Cl.0.2H$_2$O: Calcd.: C, 74.08; H, 5.83; N, 3.32 Found: C, 73.97; H, 5.81; N, 3.26

Example 4

N-[2,6-Bis(1-methylethyl)phenyl]-5-chloro-3-phenyl-2-benzofuranacetamide m.p. 260–262° C. (recrystallized from ethyl acetate-isopropyl ether)

NMR (200 MHz, CDCl$_3$) ppm: 1.10(12H,d,J=6.8 Hz), 2.94(2H,m), 4.03(2H,s), 6.90–7.70(12H,m)

Elemental Analysis for C$_{28}$H$_{28}$NO$_2$: Calcd.: C, 75.41; H, 6.33; N, 3.14 Found: C, 75.13; H, 6.39; N, 3.22

Example 5

5-Chloro-N-(2,6-dimethoxyphenyl)-3-phenyl-2-benzofuran acetamide m.p. 253–254.5° C. (recrystallized from ethyl acetate-isopropyl ether)

NMR (200 MHz, CDCl$_3$) ppm: 3.77(6H,s), 3.95(2H,s), 6.55(2H,d,J=8.4 Hz), 6.87(1H,bs), 7.10–7.70(9H,m)

Elemental Analysis for C$_{24}$H$_{20}$NO$_4$Cl: Calcd.: C, 68.33; H, 4.78; N, 3.32 Found: C, 68.14; H, 4.91; N, 3.38

Example 6

N-[2,6-Bis(1-methylethyl)phenyl]-5-chloro-1-methyl-3-phenyl-2-indoleacetamide

To a solution of 5-chloro-1-methyl-3-phenylindole-2-acetic acid (150 mg) in anhydrous THF (5 ml) were added oxalyl chloride (0.10 ml) and DMF (one drop) at room temperature, then the mixture was stirred for 0.5 hour. From the mixture was distilled off the solvent, and the residue was dissolved in dichloromethane (3 ml). This solution was added to a solution of 2,6-diisopropylaniline (0.15 ml) and triethylamine (0.40 ml) in dichloromethane (5 ml), then the mixture was stirred for one hour at room temperature. The solvent was distilled off. To the residue was added ethyl acetate. The mixture was washed with water, dilute hydrochloric acid, water, an aqueous solution of sodium hydrogencarbonate and water, successively, which was then dried, followed by distilling off the solvent to give the title compound as colorless crystals (74 mg).

m.p. 279–280° C. (recrystallized from ethyl acetate-isopropyl ether)

NMR (200 MHz, CDCl$_3$) ppm: 1.01(12H,d,J=7.0 Hz), 2.70(2H,m), 3.87(3H,s), 4.10(2H,s), 6.54(1H,bs), 7.05–7.65 (11H,m)

Elemental Analysis for $C_{29}H_{31}N_2OCl$: Calcd.: C, 75.88; H, 6.81; N, 6.10 Found: C, 75.74; H, 6.61; N, 5.92

In Examples 7 to 10, substantially the same reaction as in Example 6 was conducted, by employing indole-2-acetic acid and aniline respectively corresponding to the respective title compound as starting compounds, to obtain the objective compounds.

Example 7

N-[2,6-Bis(1-methylethyl)phenyl]-5-chloro-1-methyl-3-(2-methylphenyl)-2-indoleacetamide m.p. 266–267° C. (recrystallized from THF-isopropyl ether)

NMR (200 MHz,CDCl$_3$) ppm: 1.02(12H,t like,J=6.8 Hz), 2.17(3H,s), 2.70(2H,m), 3.78(1H,d,J=16 Hz), 3.88(3H,s), 3.91(1H,d,J=16 Hz), 6.54(1H,bs), 7.05–7.40(10H,m)

Elemental Analysis for $C_{30}H_{33}N_2OCl.0.2H_2O$: Calcd.: C, 75.59; H, 7.06; N, 5.88 Found: C, 75.70; H, 7.04; N, 5.75

Example 8

5-Chloro-N-(2,6-dimethoxyphenyl)-1-methyl-3-(2-methylphenyl)-2-indoleacetamide m.p. 191–193° C. (recrystallized from ethyl acetate-isopropyl ether)

NMR (200 MHz,CDCl$_3$) ppm: 2.18(3H,s), 3.75(6H,s), 3.78(2H,bs), 3.87(3H,s), 6.51(1H,bs), 6.53(2H,d,J=8.4 Hz), 7.10–7.40(8H,m)

Elemental Analysis for $C_{26}H_{25}N_2O_3Cl$: Calcd.: C, 69.56; H, 5.61; N, 6.24 Found: C, 69.35; H, 5.64; N, 6.23

Example 9

N-[2,6-Bis(1-methylethyl)phenyl]-5-chloro-3-(2-methoxyphenyl)-1-methyl-2-indoleacetamide m.p. 270–273° C. (recrystallized from ethyl acetate-isopropyl ether)

NMR (200 MHz,CDCl$_3$) ppm: 0.80–1.10(12H,m), 2.63 (2H,m), 3.62(3H,s), 3.84(5H,s like), 7.00–7.50(11H,m)

Elemental Analysis for $C_{30}H_{33}N_2O_2Cl$: Calcd.: C, 73.68; H, 6.80; N, 5.73 Found: C, 73.54; H, 6.88; N, 5.60

Example 10

5-Chloro-N-(2,6-dimethoxyphenyl)-3-(2-methoxyphenyl)-1-methyl-2-indoleacetamide m.p. 160° C. (recrystallized from ethyl acetate-isopropyl ether)

NMR (200 MHz,CDCl$_3$) ppm: 3.74(9H,s), 3.85(5H,s like), 6.53(2H,d,J=8.4 Hz), 6.95–7.45(9H,m)

Elemental Analysis for $C_{26}H_{25}N_2O_4Cl$: Calcd.: C, 67.17; H, 5.42; N, 6.03 Found: C, 67.14; H, 5.59; N, 5.78

Example 11

N-[2,6-Bis(1-methylethyl)phenyl]-N'-[5-chloro-3-(2-methylphenyl)-2-benzofuryl]urea To a suspension of 5-chloro-3-(2-methylphenyl) benzofuran-2-carboxylic acid (300 mg) in anhydrous benzene (10 ml) were added diphenyl phosphoryl azide (0.33 ml) and triethylamine (0.16 ml). The mixture was stirred for 15 minutes at room temperature, then heated under reflux for one hour. To the reaction mixture (containing 5-chloro-3-phenylbenzofuran-2-isocyanate) was added 2,6-diisopropyl aniline (0.3 ml), and the mixture was stirred with heating under reflux for 0.5 hour, then the solvent was distilled off. To the residue was added ethyl acetate, which was washed with water, dilute hydrochloric acid, water, an aqueous solution of sodium hydrogencarbonate and water, successively, followed by drying and distilling off the solvent to give the title compound as colorless crystals (217 mg).

m.p. 240–240.5° C. (recrystallized from ethyl acetate-isopropyl ether)

NMR (200 MHz,CDCl$_3$) ppm: 0.9–1.30(12H,m), 2.10 (1.5H,s), 2.29(1.5H,s), 3.09(2H,m), 6.00(0.5H,bs), 6.11 (0.5H,bs), 6.79(0.5H,s), 7.06(0.5H,bs), 7.10–7.40(10H,m)

Elemental Analysis for $C_{28}H_{29}N_2O_2Cl$: Calcd.: C, 72.95; H, 6.34; N, 6.08 Found: C, 73.01; H, 6.32; N, 5.78

Example 12

N-[5-Chloro-3-(2-methylphenyl)-2-benzofuryl]-N'-(2,4-difluorophenyl)urea

Using 2,4-difluoroaniline in place of 2,6-diisopropylaniline in Example 11, substantially the same reaction as in Example 11 was carried out to afford the title compound as colorless crystals.

m.p. about 230° C. (decomp.) (recrystallized from ethyl acetate-isopropyl ether)

NMR (200 MHz,CDCl$_3$) ppm: 2.24(3H,s), 6.75–6.90(3H, m), 6.95–7.50(7H,m), 7.85(1H,bs), 7.90–8.10(1H,m)

Elemental Analysis for $C_{22}H_{15}N_2O_2ClF_2.0.3H_2O$: Calcd.: C, 63.18; H, 3.76; N, 6.70 Found: C, 63.19; H, 3.88; N, 6.62

Example 13

N-[5-Chloro-3-(2-methylphenyl)-2-benzofurylmethyl]-N'-(2,4-difluorophenyl)urea

To a suspension of 5-chloro-3-(2-methylphenyl) benzofuran-2-acetic acid (300 mg) in anhydrous benzene (10 ml) were added diphenyl phosphoryl azide (0.33 ml) and triethylamine (0.16 ml). The mixture was stirred for 15 minutes at room temperature, then heated under reflux for one hour. To this reaction mixture {containing 2-[5-chloro-3-(2-methylphenyl)benzofuryl]methyl isocyanate} was added 2,4-difluoroaniline (0.30 ml), and the mixture was stirred with heating under reflux for 0.5 hour. The solvent was distilled off. To the residue was added ethyl acetate, which was washed with water, dilute hydrochloric acid, water, an aqueous solution of sodium hydrogencarbonate and water, successively, followed by drying and distilling off the solvent. The residue was purified by means of a silica gel (30 g) column chromatography (hexane-ethyl acetate=3:1) to afford the title compound as colorless crystals (63 mg).

m.p. 178–180° C. (recrystallized from ethyl acetate-hexane)

NMR (200 MHz,CDCl$_3$) ppm: 2.12(3H,s), 4.44(2H,s like), 5.49(1H,bs), 6.65–6.80(3H,m), 7.10–7.35(7H,m), 7.70–7.90(1H,m)

Elemental Analysis for $C_{23}H_{17}N_2O_2ClF_2$: Calcd.: C, 64.72; H, 4.01; N, 6.56 Found: C, 64.46; H, 4.36; N, 6.32

Example 14

N-[5-Chloro-1-methyl-3-phenyl-2-indolylmethyl]-N'-(3-isopropoxyphenyl)urea

Substantially the same reaction as in Example 13 was carried out, using 5-chloro-3-phenylbenzofuran-2-acetic acid in place of 5-chloro-3-(2-methylphenyl)benzofuran-2-acetic acid, and 3-isopropoxyaniline in place of 2,4-difluoroaniline to afford the title compound as colorless crystals.

m.p. 218–220° C. (recrystallized from acetone-ethyl ether)

NMR (200 MHz, CDCl$_3$) ppm: 1.30(6H,d,J=6 Hz), 3.18 (3H,s), 4.49(1H,m), 4.71(2H,s), 4.8(1H,b), 6.2(1H,b), 6.60–6.70(2H,m), 6.84–6.86(1H,m), 7.12–7.51(8H,m), 7.58 (1H,d,J=2 Hz).

Elemental Analysis for $C_{26}H_{26}N_3O_2Cl$: Calcd.: C, 69.71; H, 5.85; N, 9.38 Found: C, 69.61; H, 5.82; N, 9.37

Example 15

5-Chloro-N-(2,6-diethoxyphenyl)-3-(2-methoxyphenyl)-1-methyl-2-indoleacetamide

5-Chloro-3-(2-methoxyphenyl)-1-methylindole-2-acetic acid was reacted with 2,6-diethoxyaniline by a method similar to Example 6 to give the title compound as colorless crystals.

m.p. 180–183° C. (recrystallized from ethyl acetate-isopropyl ether)

NMR (200 MHz, CDCl$_3$) ppm: 1.25(4H,t,J=6.8 Hz), 1.39 (2H,t,J=6.9 Hz), 3.73(3H,s), 3.86(3H,s), 3.96(2.7H,q,J=6.8 Hz), 4.08(1.3H,q,J=6.9 Hz), 6.49(1.3H,d,J=8.4 Hz), 6.58 (0.7H,d,J=8.6 Hz), 6.90–7.50 (9H,m)

Example 16

5-Chloro-N-(2,6-diethoxyphenyl)-3-(2-methylphenyl)-2-benzofuranacetamide 2,6-Diethoxyaniline was used in place of 2,6-diisopropylaniline in Example 1, and treated by a method similar to Example 1 to give the title compound as colorless crystals.

m.p. 145–147° C. (recrystallized from ethyl ether-isopropyl ether)

NMR (200 MHz, CDCl$_3$) ppm: 1.28(5H,t,J=7.0 Hz), 1.39(1H,t,J=7.0 Hz), 2.20(3H,s), 3.75(2H,bs), 3.98(3.3H,q, J=7.0 Hz), 4.08(0.7H,q,J=7.0 Hz), 6.51(1.7H,d,J=8.4 Hz), 6.58(0.3H,d,J=8.4 Hz), 6.87(1H,bs), 7.04–7.47(8H,m)

Example 17

5-Chloro-3-(2-methylphenyl)-N-(2,4,6-trifluorophenyl)-2-benzofuranacetamide 2,4,6-Trifluoroaniline was used in place of 2,6-diisopropylaniline in Example 1, and treated by a method similar to Example 1 to give the title compound as colorless crystals.

m.p. 193–194° C. (recrystallized from ethyl acetate-isopropyl ether)

NMR (200 MHz, CDCl$_3$) ppm: 2.20(3H,s), 3.82(2H,d,J= 1.8 Hz), 6.65–6.80(2H,m), 6.98(1H,bs), 7.23–7.51(7H,m)

2,4,6-Trifluoroaniline, 2,6-dimethoxyaniline and 2,6-diethoxyaniline were used in place of 2,6-diisopropylaniline in Example 11, and treated by a method similar to Example 11 to give the compounds of Example 18, 19 and 20, respectively.

Example 18

N-[5-Chloro-3-(2-methylphenyl)-2-benzofuryl]-N'-(2,4,6-trifluorophenyl)urea m.p. 224–226° C. (recrystallized from ethyl acetate-isopropyl ether)

NMR (200 MHz, CDCl$_3$) ppm: 2.27(3H,s), 6.70(2H,t,J= 8.0 Hz), 7.15–7.44(7H,m), 7.73(1H,s), 8.46(1H,s)

Example 19

N-[5-Chloro-3-(2-methylphenyl)-2-benzofuryl]-N'-(2,6-dimethoxyphenyl)urea m.p. 254–256° C. (recrystallized from THF-isopropyl ether)

NMR (200 MHz, CDCl$_3$) ppm: 2.24(3H,s), 3.69(6H,s), 6.52(1H,bs), 6.56(2H,d,J=8.4 Hz), 7.12–7.43(10H,m)

Example 20

N-[5-Chloro-3-(2-methylphenyl)-2-benzofuryl]-N'-(2,6-diethoxyphenyl)urea m.p. 210–212° C. (recrystallized from ethyl acetate-isopropyl ether)

NMR (200 MHz, CDCl$_3$) ppm: 1.28(6H,t,J=7.0 Hz), 2.21(3H,s), 3.96(4H,q,J=7.0 Hz), 6.53(1H,s), 6.55(2H,d,J= 8.0 Hz), 6.95(1H,bt), 7.07–7.44(8H,m)

In Example 21 and 22, substantially the same reaction as in Example 1 was conducted, by employing 5-chloro-3-(2-trifluoromethylphenyl)benzofuran-2-acetic acid (Reference Example 9) and anilines (2,6-diisopropylaniline and 2,6-diethoxyaniline) to obtain the title compounds.

Example 21

N-[2,6-Bis(1-methylethyl)phenyl]-5-chloro-3-(2-trifluoromethylphenyl)-2-benzofuranacetamide m.p. 233–234° C. (recrystallized from ethyl acetate)

NMR (200 MHz, CDCl$_3$) ppm: 1.13(12H,dd,J=6.8, 3.2 Hz), 2.90–3.08(2H,m), 3.79(2H,dd,J=24.0, 16.4 Hz), 6.96–7.04(2H,m), 7.12–7.48(6H,m), 7.56–7.69(2H,m), 7.88 (1H, dd, J=6.6,2.0 Hz)

Elemental Analysis for $C_{29}H_{27}NO_2ClF_3$: Calcd.: C, 67.77; H, 5.29; N, 2.73 Found: C, 67.61; H, 5.29; N, 2.56

Example 22

5-Chloro-N-(2,6-diethoxyphenyl)-3-(2-trifluoromethylphenyl)-2-benzofuranacetamide m.p. 133.6–134.2° C. (recrystallized from hexane-isopropyl ether)

NMR (200 MHz, CDCl$_3$) ppm: 1.26(6H,t,J=7.0 Hz), 3.57–3.90 (2H,m), 3.98(4H,q,J=7.0 Hz), 6.52(2H,d,J=8.4 Hz), 6.71 (1H,S), 6.90(1H,bs), 7.06–7.28(3H,m), 7.38–7.52 (2H,m), 7.52–7.68(2H,m), 7.84(1H,dd,J=7.2, 1.8 Hz)

Elemental Analysis for $C_{27}H_{23}NO_4ClF_3$: Calcd.: C, 62.61; H, 4.48; N, 2.70 Found: C, 62.22; H, 4.43; N, 2.56

In Example 23 and 24, substantially the same reaction as in Example 11 was conducted, by employing 5-chloro-3-(2-trifluoromethylphenyl)benzofuran-2-carboxylic acid (Reference Example 8) and anilines (2,6-diisopropylaniline and 2,6-diethoxyaniline) to obtain the title compounds.

Example 23

N-[2,6-Bis(1-methylethyl)phenyl]-N'-[5-chloro-3-(2-trifluoromethylphenyl)-2-benzofuryl]urea m.p. 223.6–224° C. (recrystallized from ethyl acetate)

NMR (200 MHz, $CDCl_3$) ppm: 0.69–1.36(12H,m), 2.80–3.44 (2H,m), 5.90, 6.02(total 1H, each bs), 6.54, 7.00–7.95 (total 11H,bs and m)

Elemental Analysis for $C_{28}H_{26}N_2O_2ClF_3$: Calcd.: C, 65.31; H, 5.09; N, 5.44 Found: C, 64.93; H, 5.09; N, 5.30

Example 24

N-[5-Chloro-3-(2-trifluoromethylphenyl)-2-benzofuryl]-N'-(2,6-diethoxyphenyl)urea m.p. 184–185° C. (recrystallized from ethyl acetate)

NMR (200 MHz, $CDCl_3$) ppm: 1.27(6H,t,J=7.0 Hz), 3.90–4.04(4H,m), 6.40(1H,bs), 6.56(2H,d,J=8.4 Hz), 7.06–7.24(4H,m) 7.38(1H,d,J=9.0 Hz), 7.47–7.71(3H,m), 7.80(1H,d.J=6.6 Hz)

Elemental Analysis for $C_{26}H_{22}N_2O_4ClF_3$: Calcd.: C, 60.18; H, 4.27; N, 5.40 Found: C, 60.16; H, 4.38; N, 5.36

Reference Example 1

5-Chloro-3-phenylbenzofuran-2-carboxylic acid

Step 1

To a solution of 4-chloro-2-benzoylphenol (1.95 g) in DMF (30 ml) was added sodium hydride (60% oil) (400 mg). The mixture was stirred for 30 minutes at room temperature, to which was then added methyl ester of bromoacetic acid (1.0 ml). The mixture was stirred for 2 hours under cooling with ice-water. The reaction mixture was concentrated, to which was added ethyl acetate. The mixture was washed with water, which was then dried. The solvent was distilled off, and the residue was purified by means of a silica gel (40 g) column chromatography (hexane-ethyl acetate=3:1) to afford methyl ester of 4-chloro-2-benzoylphenoxyacetic acid as colorless crystals (2.21 g).

m.p. 71–72° C. (recrystallized from ethyl ether-hexane)

NMR (200 MHz,$CDCl_3$) ppm: 3.70(3H,s), 4.54(2H,s), 6.81(1H,d like,J=9.2 Hz), 7.35–7.60(5H,m), 7.85(2H,d like, 7.0 Hz)

Elemental Analysis for $C_{16}H_{13}O_4Cl$: Calcd.: C, 63.06; H, 4.30 Found: C, 63.04; H, 4.27

Step 2

To a solution of the compound (2.1 g) obtained in Step 1 was added 1,8-diazabicyclo[5.4.0]undec-7-ene (2.1 ml). The mixture was stirred with heating under reflux for 2 hours. The reaction mixture was diluted with ethyl acetate, washed with water and dried. The solvent was then distilled off to give methyl ester of 5-chloro-3-benzofuran-2-carboxylic acid as colorless crystals (1.32 g).

m.p. 103–105° C. (recrystallized from ethyl ether-hexane)

NMR (200 MHz,$CDCl_3$) ppm: 3.88(3H,s), 7.30–7.65(8H, m)

Elemental Analysis for $C_{16}H_{11}O_3Cl.0.3H_2O$: Calcd.: C, 65.79; H, 4.00 Found: C, 65.88; H, 4.15

Step 3

To a solution of the compound (1.2 g) obtained in Step 2 dissolved in a mixture of methanol (20 ml) and THF (20 ml) was added 2N—NaOH (5.0 ml). The mixture was stirred for 2 hours at room temperature. The reaction mixture was concentrated, to which was added water, followed by washing with ethyl acetate. The aqueous layer was made acidic with dilute hydrochloric acid, which was subjected to extraction with ethyl acetate. The extract was washed with water, which was then dried. The solvent was distilled off to give the title compound as colorless crystals (0.69 g).

m.p. 247–248° C. (recrystallized from THF-isopropyl ether)

NMR (200 MHz,$CDCl_3$) ppm: 7.35–7.60(8H,m)

Elemental Analysis for $C_{15}H_9O_3Cl$: Calcd.: C, 66.07; H, 3.33 Found: C, 65.77; H, 3.17

Reference Example 2

5-Chloro-3-phenylbenzofuran-2-acetic acid

Step 1

To a solution of 5-chloro-3-phenylbenzofuran-2-carboxylic acid (0.66 g) in anhydrous THF (15 ml) were added oxalyl chloride (0.30 ml) and DMF (one drop) at room temperature. The mixture was stirred for 0.5 hour. The solvent was distilled off, and the residue (containing the acid chloride) was dissolved in anhydrous THF (10 ml). To this solution was added an ethyl ether solution of diazomethane (prepared from 1.5 g of N-nitrosomethyl urea). The mixture was stirred for 0.5 hour at room temperature. The solvent was distilled off, and the residue (containing the diazoketone compound) was dissolved in methanol (20 ml). To the solution was added portionwise silver oxide ($Ag_2O$) (0.20 g), while stirring at 50° C. This mixture was stirred with heating under reflux for 3 hours, which was then subjected to filtration with celite. From the filtrate was distilled off the solvent. The residue was purified by means of a silica gel (30 g) column chromatography (hexane-ethyl acetate=5:1) to afford methyl ester of 5-chloro-3-phenylbenzofuran-2-acetic acid as a pale yellow oily product (0.44 g)

$^1$H-NMR (200 MHz, $CDCl_3$) ppm: 3.76(3H,s), 3.87(2H, s), 7.20–7.30(1H,m), 7.35–7.60(7H,m).

Step 2

To a solution of the compound (0.44 g) obtained in Step 1 in methanol (10 ml) was added 1N—NaOH (2 ml), which was stirred for 2 hours at room temperature. The reaction mixture was concentrated, to which was added water, followed by washing with ethyl acetate. The aqueous layer was made acidic with dilute hydrochloric acid, which was subjected to extraction with ethyl acetate. The extract was washed with water, which was then dried. The solvent was distilled off to give the title compound as colorless crystals (0.25 g).

m.p. 194–195° C. (recrystallized from ethyl ether-hexane)

NMR (200 MHz, $CDCl_3$) ppm: 3.91(2H,s), 7.20–7.60 (8H,m)

Elemental Analysis for $C_{16}H_{11}O_3Cl$: Calcd.: C, 67.03; H, 3.87 Found: C, 67.09; H, 3.76

Reference Example 3

5-Chloro-3-(2-methylphenyl)benzofuran-2-carboxylic acid

Using 4-chloro-2-(2-methylbenzoyl)phenol in place of 4-chloro-2-benzoylphenol in Reference Example 1, substantially the same reactions as in Step 1 to Step 3 of Reference Example 1 were conducted to give the title compound. The compounds obtained in the respective steps and their physico-chemical data are shown below.
Step 1

4-Chloro-2-(2-methylbenzoyl)phenoxyacetic acid methyl ester m.p. 81–83° C. (recrystallized from ethyl ether-hexane)

NMR (200 MHz, CDCl$_3$) ppm: 2.53(3H,s), 3.70(3H,s), 4.47(2H,s), 6.79(1H,d,J=8.4 Hz), 7.10–7.45(6H,m)

Elemental Analysis for C$_{17}$H$_{15}$O$_4$Cl: Calcd.: C, 64.06; H, 4.74 Found: C, 64.08; H, 4.69

Step 2

5-Chloro-3-(2-methylphenyl)benzofuran-2-carboxylic acid methyl ester a pale yellow oily substance NMR (200 MHz, CDCl$_3$) ppm: 2.16(3H,s), 3.82(3H,s), 7.20–7.60(7H,m)

Step 3 (title compound)

m.p. 212–214° C. (recrystallized from ethyl acetate-hexane)

NMR (200 MHz, CDCl$_3$) ppm: 2.16(3H,s), 7.20–7.60 (7H,m), 9.00(1H,bs)

Elemental Analysis for C$_{16}$H$_{11}$O$_3$Cl: Calcd.: C, 67.03; H, 3.87 Found: C, 66.86; H, 3.93

Reference Example 4

5-Chloro-3-(2-methylphenyl)benzofuran-2-acetic acid

Using 5-chloro-3-(2-methylphenyl)benzofuran-2-carboxylic acid in place of 5-chloro-3-phenylbenzofuran-2-carboxylic acid in Reference Example 2, substantially the same reactions as in Step 1 and Step 2 of Reference Example 2 were conducted to give the title compound. The compounds obtained in the respective steps and their physico-chemical data are shown below.
Step 1

5-Chloro-3-(2-methylphenyl)benzofuran-2-acetic acid methyl ester a pale yellow oily substance NMR (200 MHz, CDCl$_3$) ppm: 2.18(3H,s), 3.69(5H,s like), 7.19–7.45(7H,m)

Step 2 (title compound)

m.p. 135–136° C. (recrystallized from ethyl ether-hexane)

NMR (200 MHz, CDCl$_3$) ppm: 2.17(3H,s), 3.73(2H,s), 7.20–7.45(7H,m)

Elemental Analysis for C$_{17}$H$_{13}$O$_3$Cl: Calcd.: C, 67.89; H, 4.36 Found: C, 67.85; H, 4.39

Reference Example 5

5-Chloro-1-methyl-3-phenylindole-2-acetic acid

Step 1

To a solution of γ-phenyl acetoacetic acid ethyl ester (2.88 g) in a mixture of acetic acid (30 ml) and water (10 ml) were added sodium acetate (1.83 g) and 1-(4-chlorophenyl)-1-methyl hydrazine hydrochloride (2.73 g) {prepared from 4-chloro-N-methyl-N-nitroso aniline by subjecting to reduction with zinc powder in a mixture of acetic acid and water [m.p.171–174° C.; NMR (200 MHz, DMSO-d$_6$) ppm: 3.14 (3H,s), 7.20(2H,d,J=9 Hz), 7.29(2H,d,J=9 Hz)]}. The mixture was stirred for 15 minutes at room temperature, then for 20 minutes at 110° C. The reaction mixture was concentrated, which was dissolved in ethyl acetate. The solution was washed with water, dilute hydrochloric acid, water, an aqueous solution of sodium hydrogencarbonate and water, successively, which was then dried, followed by distilling off the solvent. The residue was purified by means of a silica gel (30 g) column chromatography (hexane-ethyl acetate=4:1) to give ethyl ester of 5-chloro-1-methyl-3-phenylindole-2-acetic acid as an oily substance (4.34 g). [NMR (200 MHz, CDCl$_3$) ppm: 1.29(3H,t,J=7 Hz), 3.76 (3H,s), 3.86(2H,s), 4.24(2H,q,J=7 Hz), 7.17–7.62(8H,m)]

Step 2

A mixture of the compound (4.20 g) obtained in Step 1, ethanol (70 ml) and NaOH (20 ml) was stirred for 14 hours at room temperature. The reaction mixture was concentrated, to which was added water. The mixture was washed with ethyl acetate. The aqueous layer was made acidic with dilute hydrochloric acid, which was subjected to extraction with ethyl acetate. The extract was washed with water and dried. The solvent was distilled off to give the title compound as pale yellow crystals (2.73 g).

m.p. 141–142° C. (recrystallized from ethyl acetate-hexane)

NMR (200 MHz, CDCl$_3$) ppm: 3.78(3H,s), 3.93(2H,s), 7.24–7.61(8H,m)

Elemental Analysis for C$_{17}$H$_{14}$NO$_2$Cl: Calcd.: C, 68.12; H, 4.71; N, 4.67 Found: C, 68.01; H, 4.69; N, 4.55

Reference Example 6

5-Chloro-1-methyl-3-(2-methylphenyl)indole-2-acetic acid

Step 1

Using, in place of γ-phenyl acetoacetic acid ethyl ester in Step 1 of Reference Example 5, γ-(2-methylphenyl) acetoacetic acid ethyl ester {prepared from 2-methylphenyl acetic acid by subjecting to carbon-elongation reaction in THF using N-carbonyl imidazole and magnesium salt of ethylmalonic acid [NMR (200 MHz, CDCl$_3$) ppm: 1.26(3H, t,J=7 Hz), 2.25(3H,s), 3.43(2H,s), 3.85(2H,s), 4.17(2H,q, J=7 Hz), 7.11–7.20(4 Hz t,J=7 Hz)]}, substantially the same reaction as in Step 1 of Reference Example 5 was conducted to give ethyl ester of 5-chloro-1-methyl-3-(2-methylphenyl) indole-2-acetic acid as an oily product [NMR (200 MHz, CDCl$_3$) ppm: 1.22(3H,t,J=7 Hz), 2.12(3H,s), 3.67,3.68(each 1H,s), 3.76(3H,s), 4.14(2H,q,J=7 Hz), 7.15–7.35(7H,m)].

Step 2

The compound obtained in Step 1 was subjected to hydrolysis in substantially the same manner as in Step 2 of Reference Example 5 to give the title compound as pale yellow crystals.

m.p. 154.5–155.5° C. (recrystallized from ethyl acetate-isopropyl ether)

NMR (200 MHz, CDCl$_3$) ppm: 2.11(3H,s), 3.73,3.74 (each 1H,s), 3.76(3H,s), 7.15–7.31(7H,m)

Elemental Analysis for C$_{18}$H$_{16}$NO$_2$Cl: Calcd.: C, 68.90; H, 5.14; N, 4.46 Found: C, 68.96; H, 5.14; N, 4.39

Reference Example 7

5-Chloro-3-(2-methoxyphenyl)-1-methylindole-2-acetic acid

Step 1

Using, in place of γ-phenylacetoacetic acid ethyl ester in Step 1 of Reference Example 5, ethyl ester of γ-(2-methoxyphenyl)acetoacetic acid {prepared from 2-methoxy phenylacetic acid by subjecting to carbon-elongation reaction in THF using N,N-carbonylimidazole and magnesium salt of ethyl malonic acid [NMR (200 MHz, CDCl$_3$) ppm: 1.26(3H,t,J=7 Hz), 3.45(2H,s), 3.78(2H,s), 3.82(3H,s), 4.17 (2H,q,J=7 Hz), 6.87–7.32(4H,m)]}, substantially the same reaction as in Step 1 of Reference Example 5 was conducted to give ethyl ester of 5-chloro-3-(2-methoxyphenyl)-1-methylindole-2-acetic acid as pale yellow crystals.

m.p. 94–95° C. (recrystallized from ethyl ether-hexane)

NMR (200 MHz, CDCl$_3$) ppm: 1.26(3H,t,J=7.0 Hz), 3.74(3H,s), 3.76(3H,s), 4.19(2H,q,J=7.0 Hz), 6.95–7.45(7H, m)

Elemental Analysis for C$_{20}$H$_{20}$N$_3$Cl: Calcd.: C, 67.13; H, 5.63; N, 3.91 Found: C, 67.20; H, 5.58; N, 3.94

Step 2

Using the compound obtained in Step 1, hydrolysis was conducted in substantially the same manner as in Step 2 of Reference Example 5 to thereby afford the title compound as colorless crystals.

m.p. 153–154° C. (recrystallized from ethyl ether-hexane)

NMR (200 MHz, CDCl$_3$) ppm: 3.73(3H,s), 3.76(3H,s), 3.78(2H,s), 7.00–7.45(7H,m)

Elemental Analysis for C$_{18}$H$_{16}$NO$_3$Cl: Calcd.: C, 65.56; HI 4.89; N, 4.25 Found: C, 65.62; H, 4.98; N, 4.22

Reference Example 8

5-Chloro-3-(2-trifluoromethylphenyl)benzofuran-2-carboxylic acid

Using 4-chloro-2-(2-trifluoromethylbenzoyl)phenol [prepared from 2-bromo-4-chloro-(2-methoxyethoxy)methoxybenzene and ortho-(trifluoromethyl)benzaldehyde as the starting materials: m.p. 71–72° C. (recrystallized from hexane-isopropyl ether)] in place of 4-chloro-2-benzoylphenol in Reference Example 1, substantially the same reations as in Step 1 to Step 3 of Reference Example 1 were conducted to give the title compound. The compounds obtained in the respective steps and their physicochemical data are shown below.

Step 1

4-Chloro-2-(2-trifluoromethylbenzoyl)phenoxyacetic acid methyl ester m.p. 133–134° C. (recrystallized from ethyl acetate)

NMR (200 MHz, CDCl$_3$) ppm: 3.67(3H,s), 4.37(2H,s), 6.76(1H,d,J=8.8 Hz), 7.38–7.50(2H,m), 7.51–7.60(2H,m), 7.70–7.80(2H,m)

Step 2

5-Chloro-3-(2-trifluoromethylphenyl)benzofuran-2-carboxylic acid methyl ester m.p. 104–106° C. (recrystallized from hexane)

NMR (200 MHz, CDCl$_3$) ppm: 3.77(3H,s), 7.26(1H,s), 7.36(1H,d,J=6.6Hz), 7.45(1H,dd,J=9.0,2.2 Hz), 7.55–7.72 (3H,m), 7.85(1H,dd,J=6.8,2.0 Hz)

Step 3 (title compound)

m.p. 205–208° C. (recrystallized from hexane)

NMR (200 MHz, CDCl$_3$) ppm: 7.26(1H,s), 7.36(2H,dd, J=6.2,2.2 Hz), 7.47(1H,dd,J=9.0,2.0 Hz), 7.53–7.71(3H,m), 7.84(1H,dd,J=6.8,2.4 Hz)

Elemental analysis for C$_{16}$H$_8$O$_3$ClF$_3$: Calcd.: C, 56.41; H, 2.37 Found: C, 56.22; H, 2.35

Reference Example 9

5-Chloro-3-(2-trifluoromethylphenyl)benzofuran-2-acetic acid

Using 5-Chloro-3-(2-trifluoromethylphenyl)benzofuran-2-carboxylic acid in place of 5-chloro-3-phenylbenzofuran-2-carboxylic acid in Reference Example 2, substantially the same reactions as in Step 1 and Step 2 of Reference Example 2 were conducted to give the title compound. The compounds obtained in the respective steps and their physicochemical data are shown below.

Step 1

5-Chloro-3-(2-trifluoromethylphenyl)benzofuran-2-acetic acid methyl ester a pale yellow oily substance NMR (200 MHz, CDCl$_3$) ppm: 3.69(3H,s), 3.77(2H,s), 7.13(1H,d,J=2.2 Hz), 7.26(1H,dd,J=8.8,2.0 Hz), 7.32–7.70 (4H,m), 7.83(1H,dd,J=7.2,2.0 Hz)

Step 2 (title compound)

a pale yellow oily substance

NMR (200 MHz, CDCl$_3$) ppm: 3.68(2H,dd,J=27.6, 17.0 Hz), 7.14(1H,d,J=2.0 Hz), 7.26(1H,dd,J=9.2,2.0 Hz), 7.32–7.66(4H,m), 7.84(1H,dd,J=6.8,2.2 Hz)

What is claimed is:

1. A compound represented by the formula

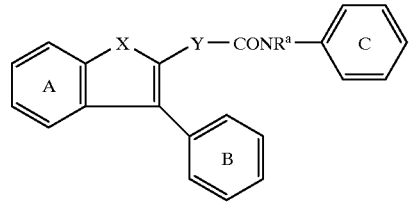

wherein rings, A, B and C, are respectively a benzene ring which may be substituted with one to four substituents selected from the group consisting of (i) a halogen, (ii) an optionally halogenated C$_{1-4}$ alkyl, (iii) an optionally halogenated C$_{1-4}$ alkoxy, (iv) an amino, (v) a mono- or di-C$_{1-4}$ alkylamino, (vi) a C$_{1-3}$ acyloxy, and (vii) a hydroxyl;

X is —S—;

Y is —(CH$_2$)n— wherein n denotes one or two, or —NH—; and

R$^a$ is a hydrogen atom provided that when ring C is unsubstituted or substituted only at para-position, ring B is substituted at least at ortho-position, or a salt thereof.

2. A compound as claimed in claim 1, wherein the ring A is a benzene ring which may be substituted with one to four substituents selected from the group consisting of (i) a halogen, (ii) an optionally halogenated C$_{1-4}$ alkyl and (iii) an optionally halogenated C$_{1-4}$ alkoxy.

3. A compound as claimed in claim 1, wherein the ring A is a group of the formula:

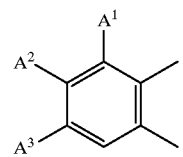

wherein A$^1$, A$^2$ and A$^3$ independently stand for a hydrogen, a halogen, an optionally halogenated C$_{1-4}$ alkyl or an optionally halogenated C$_{1-4}$ alkoxy.

4. A compound as claimed in claim 1, wherein the ring B is a benzene ring which may be substituted with one to four substituents selected from the group consisting of (i) a halogen, (ii) an optionally halogenated $C_{1-4}$ alkyl and (iii) an optionally halogenated $C_{1-4}$ alkoxy.

5. A compound as claimed in claim 1, wherein the ring B is a group of the formula:

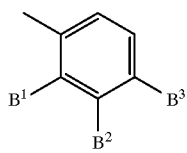

wherein $B^1$, $B^2$ and $B^3$ independently stand for a hydrogen, a halogen, an optionally halogenated $C_{1-4}$ alkyl or an optionally halogenated $C_{1-4}$ alkoxy.

6. A compound as claimed in claim 1, wherein the ring C is a group of the formula:

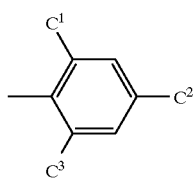

wherein $C^1$, $C^2$ and $C^3$ independently stand for a hydrogen, a halogen atom, an optionally halogenated $C_{1-4}$ alkyl, an optionally halogenated $C_{1-4}$ alkoxy or a di-$C_{1-4}$alkylamino.

7. A compound as claimed in claim 1, wherein the ring C is a ring represented by the formula:

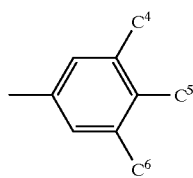

wherein $C^4$, $C^5$, and $C^6$ independently stand for a hydrogen atom, an optionally halogenated $C_{1-4}$ alkyl, an optionally halogenated $C_{1-4}$ alkoxy, a $C_{1-3}$ acyloxy or a hydroxyl.

8. A compound as claimed in claim 1, wherein Y stands for —$CH_2$—.

9. A compound as claimed in claim 1, wherein the one to four optional substituents for rings A, B, and C, are selected from the group consisting of (i) halogen.

10. A compound as claimed in claim 1, wherein the one to four optional substituents for rings A, B, and C is a (vii) hydroxyl.

11. A compound as claimed in claim 1, wherein the one to four optional substituents for rings A, B, and C are selected from the group consisting of (vi) $C_{1-3}$ acyloxy.

12. A compound as claimed in claim 1, wherein the one to four optional substituents for rings A, B, and C is a (iv) amino.

13. A compound as claimed in claim 1, wherein the one to four optional substituents for rings A, B, and C are selected from the group consisting of an (ii) optionally halogenated $C_{1-4}$ alkyl.

14. A compound as claimed in claim 1, wherein the one to four optional substituents for rings A, B, and C are selected from the group consisting of an (iii) optionally halogenated $C_{1-4}$ alkoxy.

15. A compound as claimed in claim 1, wherein the one to four optional substituents for rings A, B, and C, are selected from the group consisting of (v) a mono- or di-$C_{1-4}$ alkylamino.

16. A composition for inhibiting acyl-CoA; chlosterol acyltransferase which comprises an effective amount of a compound of the formula:

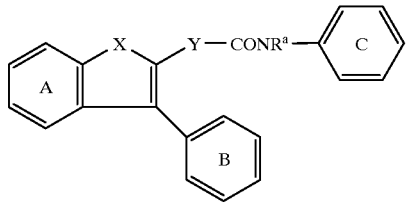

wherein rings A and B' and C', are respectively a benzene ring which may be substituted with one to four substituents selected from the group consisting of (i) a halogen, (ii) an optinally halogenated $C_{1-4}$ alkyl, (iii) an optionally halogenated $C_{1-4}$ alkoxy, (iv) an amino, (v) a mono- or di-$C_{1-4}$ alkylamino, (vi) a $C_{1-3}$ acyloxy, and (vii) a hydroxyl:

X is —S—;

Y is —($CH_2$)n— wherein n denotes one or two, or —NH—; and $R^a$ is a hydrogen atom;

provided that when ring C is unsubstituted or substituted only at para-position, ring B is substituted at least at ortho-position, or a pharmaceutically acceptable salt;

and a physiologically acceptable carrier.

* * * * *

UNITED STATES PATENT AND TRADEMARK OFFICE
CERTIFICATE OF CORRECTION

PATENT NO. : 5,929,107
DATED : July 27, 1999
INVENTOR(S) : Hideaki NATSUGARI It is certified that error appears in the above-identified patent and that said Letters Patent is hereby corrected as shown below:

Column 34, lines 25-30, delete the formula and insert therefor:

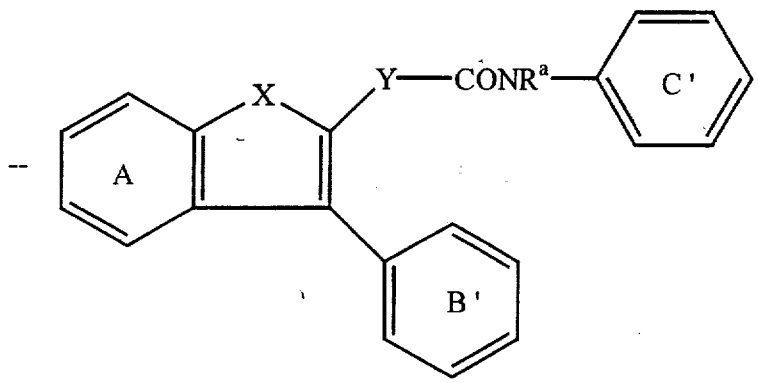

Column 34, line 43, delete "—(CH$_2$n—" and insert therefor — —(CH$_2$)$_n$—  —.

Signed and Sealed this

Fifth Day of September, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO. : 5,929,107
DATED : July 27, 1999
INVENTOR(S) : Hideaki NATSUGARI, et al.

It is certified that error appears in the above-identified patent and that said Letters Patent is hereby corrected as shown below:

Column 34, line 46, delete "C" and insert therefor --C'--.

Column 34, line 47, delete "B" and insert therefor --B'--.

Signed and Sealed this

Twenty-fourth Day of October, 2000

Attest:

Q. TODD DICKINSON

*Attesting Officer*  *Director of Patents and Trademarks*